(12) United States Patent
Adiri et al.

(10) Patent No.: US 11,961,608 B2
(45) Date of Patent: *Apr. 16, 2024

(54) IMAGE PROCESSING SYSTEMS AND METHODS FOR CARING FOR SKIN FEATURES

(71) Applicant: HEALTHY.IO LTD., Tel Aviv (IL)

(72) Inventors: Yonatan Adiri, Tel Aviv (IL); Ron Zohar, Tel Aviv (IL); Ido Omer, Tel Aviv (IL); Matan Ronen, Tel Aviv (IL); Nathaniel Bubis, Tel Aviv (IL); Nitai Fine, Tel Aviv (IL)

(73) Assignee: HEALTHY.IO LTD., Tel Aviv (IL)

( * ) Notice: Subject to any disclaimer, the term of this patent is extended or adjusted under 35 U.S.C. 154(b) by 519 days.

This patent is subject to a terminal disclaimer.

(21) Appl. No.: 17/086,800

(22) Filed: Nov. 2, 2020

(65) Prior Publication Data

US 2021/0142888 A1 May 13, 2021

Related U.S. Application Data

(60) Provisional application No. 62/933,686, filed on Nov. 11, 2019.

(51) Int. Cl.
*G16H 30/00* (2018.01)
*G06T 7/00* (2017.01)
(Continued)

(52) U.S. Cl.
CPC .......... *G16H 30/40* (2018.01); *G06T 7/0016* (2013.01); *G16H 15/00* (2018.01); *G16H 20/00* (2018.01);
(Continued)

(58) Field of Classification Search
CPC ........ G16H 30/40; G16H 40/67; G16H 15/00; G16H 20/00; G16H 80/00; G06T 7/0016;
(Continued)

(56) References Cited

U.S. PATENT DOCUMENTS

| 2008/0008370 A1* | 1/2008 | Chio | A61B 5/441 |
| | | | 600/407 |
| 2011/0109651 A1* | 5/2011 | Fairlamb | G16H 30/20 |
| | | | 382/128 |

(Continued)

FOREIGN PATENT DOCUMENTS

| WO | WO 2016/011534 A1 | 1/2016 | |
| WO | WO 2019/011523 A1 | 1/2019 | |
| WO | WO-2019011523 A1 * | 1/2019 | ........... A45D 44/005 |

*Primary Examiner* — Khai M Nguyen
(74) *Attorney, Agent, or Firm* — Finnegan, Henderson, Farabow, Garrett & Dunner, LLP

(57) ABSTRACT

Systems and methods for image processing of a skin feature may include receiving from at least one image sensor associated with a mobile communications device a first and a second images of a skin feature. The skin feature has multiple segments of differing colors and differing sizes, and the second image is captured at least a day after the first image is captured. The method may further include analyzing data associated with the first and second images to determine a condition of the skin feature based on changes over time of the multiple segments. The method may also include determining, based on the determined condition of the skin feature, a medical action for treating the skin feature during a time period. Then, the method may include causing a mobile communications device to display information indicative of the determined medical action.

20 Claims, 11 Drawing Sheets

(51) Int. Cl.
*G16H 15/00* (2018.01)
*G16H 20/00* (2018.01)
*G16H 30/40* (2018.01)
*G16H 40/67* (2018.01)
*G16H 80/00* (2018.01)

(52) U.S. Cl.
CPC ............. *G16H 40/67* (2018.01); *G16H 80/00* (2018.01); *G06T 2207/10024* (2013.01); *G06T 2207/10152* (2013.01); *G06T 2207/30088* (2013.01)

(58) Field of Classification Search
CPC . G06T 2207/10024; G06T 2207/10152; G06T 2207/30088
See application file for complete search history.

(56) References Cited

U.S. PATENT DOCUMENTS

| | | |
|---|---|---|
| 2012/0063652 A1 | 3/2012 | Chen et al. |
| 2015/0213619 A1* | 7/2015 | Nakamura ............... G06T 5/002 382/128 |
| 2016/0206205 A1* | 7/2016 | Wu ........................... G06T 7/62 |
| 2021/0142890 A1* | 5/2021 | Adiri ...................... G16H 50/20 |
| 2021/0196186 A1* | 7/2021 | Yeates ................. A61B 5/7485 |

* cited by examiner

FIG. 8B

IMAGE PROCESSING SYSTEMS AND METHODS FOR CARING FOR SKIN FEATURES

CROSS REFERENCES TO RELATED APPLICATIONS

This application claims the benefit of priority of U.S. Provisional Patent Application No. 62/933,686, filed on Nov. 11, 2019 which is incorporated herein by reference in its entirety.

BACKGROUND

I. Technical Field

The present disclosure relates generally to the field of image processing for medical purposes. More specifically, the present disclosure relates to systems, methods, and devices for using image analysis for medical examination of skin features.

II. Background Information

Computer vision may be used in medical testing to determine quantitative and qualitative clinical data. Traditionally, regulatory-approved clinical devices use dedicated hardware such as pre-calibrated scanners that operate in well-known and monitored capturing and illumination conditions, together with classifiers that operate based on the calibrated images derived by the scanners.

In recent years, smartphones have become personal mobile computers with high processing power, wireless Internet access, and high-resolution image capturing capabilities. However, turning a smartphone into a regulatory-approved clinical device is challenging for at least three main reasons. First, there may be a lack of quality uniformity of the smartphones' cameras. This can occur for a number of reasons, including the fact that the settings and imaging of each brand and model of smartphone may differ from one to the next. Even within a particular model, there may be slight variations in acquired images. Second, when using smartphones across a host of non-uniformly lit environments, local illumination conditions can lead to varying results. Third, the smartphones are typically operated by unqualified users that may have difficulties following strict medical operation procedures.

The disclosed embodiments are directed to providing new and improved ways for using personal communications devices for medical examination of skin features.

SUMMARY

Embodiments consistent with the present disclosure provide systems, methods, and devices for capturing and analyzing images for medical examination of skin features. Consistent with the disclosed embodiments, an exemplary system may receive multiple images depicting a skin feature with multiple segments of differing colors captured during a period of time. The exemplary system may determine the condition of the skin feature and provide a recommendation for continued treatment of the skin feature.

In one embodiment, a computer program product, containing instructions that when executed by at least one processor, is provided. The instructions may cause the at least one processor to carry out a method for conducting image processing of skin features. The method may include receiving, from at least one image sensor associated with a mobile communications device, a first image of the skin feature, the skin feature having multiple segments of differing colors and differing sizes; storing in at least one memory device data associated with the first image for later processing; receiving from the at least one image sensor associated with the mobile communications device a second image of the skin feature, wherein the second image is captured at least a day after the first image is captured; retrieving from the at least one memory device data associated with the first image; analyzing the retrieved data and data associated with the second image to determine a condition of the skin feature based on changes over time of the multiple segments; determining, based on the determined condition of the skin feature, at least one medical action for treating the skin feature during a time period; and causing the mobile communications device to display information indicative of the determined at least one medical action based on the changes over time of the multiple segments.

In one embodiment, a computer program product containing instructions that when executed by at least one processor is provided. The instructions may cause the at least one processor to carry out a method for conducting image processing of wound images. The method may include receiving a first image of a wound of a patient, wherein the first image is captured at an outset of a medical treatment; storing in at least one memory device data associated with the first image for later processing; receiving a second image of the wound of the patient, wherein the second image is captured at least a day after applying the medical treatment to the wound; retrieving, from the at least one memory device, data associated with the first image; analyzing the retrieved data and data associated with the second image to determine a condition of the wound; determining at least one action to alter the medical treatment based on the condition of the wound; and initiating a remedial measure associated with the at least one action to increase effectiveness of the medical treatment.

Consistent with other disclosed embodiments, systems and processing devices are configured to execute the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 8B shows additional screenshots illustrating another example GUI for displaying information indicative of determined medical action, consistent with the disclosed embodiments.

DETAILED DESCRIPTION

Figure 1:
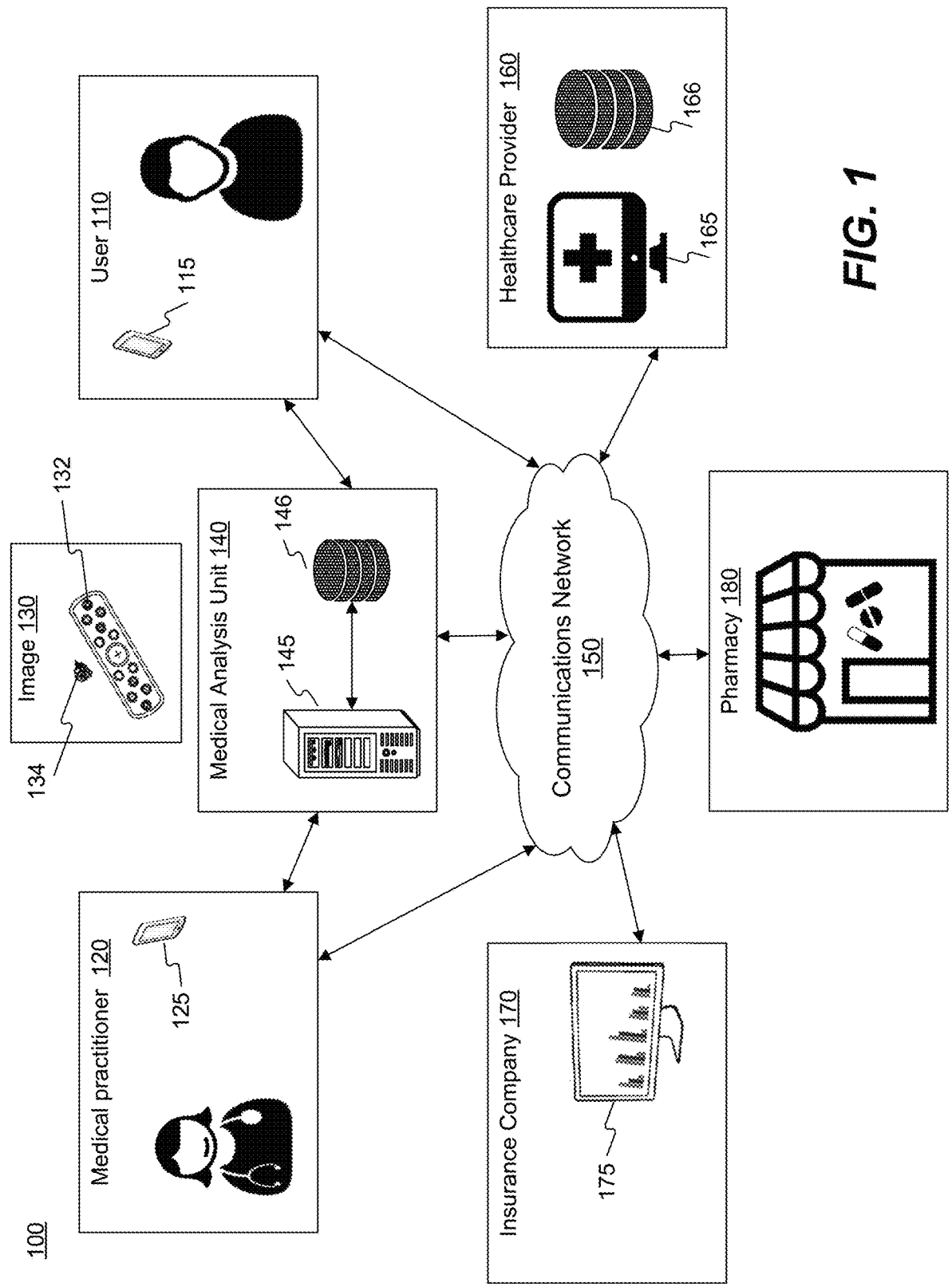
FIG. 1 is a schematic illustration of an example system that uses image data captured by mobile communications devices for medical testing, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples but is inclusive of general principles described herein in addition to the general principles encompassed by the appended claims.

The present disclosure is directed to systems and methods for processing images captured by an image sensor. As used herein, the term "image sensor" refers to any device capable of detecting and converting optical signals in the near-infrared, infrared, visible, and ultraviolet spectrums into electrical signals. Examples of image sensors may include digital cameras, phone cameras, semiconductor charge-coupled devices (CCD), active pixel sensors in complementary metal-oxide-semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct a 3D image. The image data acquired by the image sensor may be transmitted by wired or wireless transmission to a remote server.

Consistent with the present disclosure, the image sensor may be part of a camera included in a mobile communications device. The term "mobile communications device" refers to any portable device with image capturing capabilities that can communicate with a remote server over a wireless network. Examples of mobile communications devices include smartphones, tablets, smartwatches, smart glasses, wearable sensors and other wearable devices, wireless communication chipsets, user equipment (UE), personal digital assistants, and any other portable pieces of communications equipment. It is noted that the terms "handheld mobile communications device," "handheld mobile device," "mobile communications device," and "mobile device" may be used interchangeably herein and may refer to any of the variety of devices listed above.

Embodiments of the present disclosure further include analyzing images to identify a colorized surface in proximity to a medical analysis region. As used herein, the term "colorized surface" may broadly refer to any surface having planar or nonplanar properties. The colorized surface may cover or encapsulate at least a portion of a 2D object (such as a sheet of paper) or at least a portion of a 3D object (such as a box or a body part). The colorized surface may include a plurality of reference elements for enabling light and color calibration. In some embodiments, the colorized surface may be printed on a sticker or a plaster (e.g., adhesive bandage), for example, the colorized surface illustrated in FIG. 4. In other embodiments, the colorized surface may be printed or otherwise presented on a board, cardstock, plastic or any other medium adapted to serve as a reference. The image correction enabled by the colorized surface may be used to enable a color correction of an image of skin feature depicted in the image. In some embodiments, the skin feature may be skin or other tissue or anatomical feature, and the medical analysis region may include any part of the patient's body depicted in the image.

Consistent with the present disclosure, the colorized surface may enable processing of the image to determine the colors of the skin feature, irrespective of local illumination conditions and/or capturing parameters. The term "irrespective of local illumination conditions and/or capturing parameters" refers to the output of an image analysis process in which the suggested system rectifies the colors of the skin feature to remove at least some effects of local illumination, remove at least some effects of capturing parameters, or remove at least some effects of local illumination and at least some effects of capturing parameters. Effects of local illumination conditions to be removed, may include one or more of reflections, shades, light temperature (e.g., soft white, cool white, daylight), and any other condition that may impact the detection of the skin feature color. Effects of capturing parameters to be removed, may include one or more of image resolution, frame rate, gain, ISO speed, stereo base, focus, zoom, color correction profile, exposure time, shutter speed, aperture settings, ISO, distance from skin feature, angle to skin feature, and more. The removal of effects of the local illumination conditions and the effects of capturing parameters may be important to accurately determine the changes of the skin feature over time. For example, changes of the colors of an examined wound may determine its condition and its healing progress.

In some embodiments, an image correction factor may be generated based on the determined local illumination conditions and/or image capturing parameters. The image correction factor may be used to remove one or more local illumination variations and to determine illumination invariant colors of the skin feature. The image correction factor may be used to remove image capturing process effects to determine capturing process invariant colors of the skin feature. In one example, the illumination invariant colors may be used to determine a condition of the skin feature, such as a state of a wound. In another example, the invariant colors may be used to determine a condition of a tissue, such as skin, oral mucosa, nasal mucosa, and so forth. In an additional example, the invariant colors may be used to determine properties of biological material, such as a stool sample, a urine sample, a phlegm sample, a blood sample, a wax sample, and so forth.

The term "confidence level" refers to any indication, numeric or otherwise, of a level (e.g., within a predetermined range) indicative of an amount of confidence the system has that the determined colors of the skin feature are the colors of the skin feature irrespective of local illumination conditions and/or image capturing settings effects. For example, the confidence level may have a value between 1 and 10. Alternatively, the confidence level may be expressed as a percentage or any other numerical or non-numerical indication. In some cases, the system may compare the confidence level to a threshold. The term "threshold" as used herein denotes a reference value, a level, a point, or a range of values. In operation, when a confidence level of a measurement exceeds a threshold (or below it, depending on a particular use case), the system may follow a first course of action and, when the confidence level is below it (or above it, depending on a particular use case), the system may follow a second course of action. The value of the threshold may be predetermined for each type of skin feature or may be dynamically selected based on different considerations.

Reference is now made to FIG. 1, which shows an example of a system 100 that uses image analysis to complete a medical examination. System 100 may be computer-based and may include computer system components, desktop computers, workstations, tablets, handheld computing devices, memory devices, and/or internal network(s) connecting the components. System 100 may include or be connected to various network computing resources (e.g., servers, routers, switches, network connections, storage devices, etc.) for supporting services provided by system 100.

Consistent with the present disclosure, system 100 may enable user 110 to complete a medical examination. In addition, system 100 may enable a medical practitioner 120 to participate in the medical examination using a mobile communications device 125. The disclosure below that describes the functionalities of mobile communications device 115 similarly describes the functionalities of mobile communications device 125. In one embodiment, medical practitioner 120 may be a nurse that captures images of a skin feature associated with user 110. In another embodiment, medical practitioner 120 may be a physician of user 110 who receives the results of the medical examination. In the example illustrated in FIG. 1, user 110 may use mobile communications device 115 to capture an image 130 that includes a colorized surface 132 and a skin feature 134. Image data associated with image 130 may be directed (e.g., via a wired connection) or transmitted to a medical analysis unit 140 for medical testing (directly or via a communication network). Medical analysis unit 140 may include a server 145 coupled to one or more physical or virtual storage devices such as a data structure 146. System 100 may also include or be connected to a communications network 150 that facilitates communications and data exchange between different system components and the different entities associated with system 100, such as, healthcare provider 160, insurance company 170, and pharmacy 180.

According to embodiments of the present disclosure, medical analysis unit 140 may exchange data with a variety of communication devices associated with the different entities associated with system 100. The term "communication device" is intended to include all possible types of devices capable of exchanging data using communications network 150. In some examples, the communication device may include a smartphone, a tablet, a mobile station, a personal digital assistant, a desktop, a laptop, an IoT device, a dedicated terminal, a server, a cloud, and any other device that enables data communications. In one implementation, medical analysis unit 140 may receive image data from mobile communications device 115 and cause mobile communications device 115 to provide user 110 with data derived from analysis of skin feature 134. In another implementation, medical analysis unit 140 may transmit data to a communications device 165 of healthcare provider 160 for updating an electronic medical record (EMR) of user 110 stored in data structure 166. In another implementation, medical analysis unit 140 may receive information from a communications device 175 of insurance company 170. The received information may identify a group of individuals associated with a first insurance status. Thereafter, medical analysis unit 140 may initiate medical examinations to determine if there is a likelihood that the group of individuals is entitled to a second insurance status different from the first insurance status. In yet another implementation, medical analysis unit 140 may transmit a result derived from image data captured by mobile communications device 115.

Embodiments of the present disclosure may include access, or otherwise utilize one or more data structures, such as a database. As used herein, the term "data structure" may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML data structure, an RDBMS data structure, an SQL data structure or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, SharePoint, Sybase, Oracle and Neo4J. Data structures, where suitable, may also include document management systems. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Consistent with the present disclosure, server 145 may access data structure 146 to determine, for example, specific chromatic properties associated with colorized surface 132 at the time of printing of the colorized surface 132. Data structure 146 and data structure 166 may utilize a volatile or non-volatile, magnetic, semiconductor, tape, optical, removable, non-removable, other type of storage device or tangible or non-transitory computer-readable medium, or any medium or mechanism for storing information. Data structure 146 (and data structure 166 mutatis mutandis) may be part of server 145 or separate from server 145 as shown. When data structure 146 is not part of server 145, server 145 may exchange data with data structure 146 via a communication link. Data structure 146 may include one or more memory devices that store data and instructions used to perform one or more features of the disclosed embodiments.

In one embodiment, data structure 146 may include any a plurality of suitable data structures, ranging from small data structures hosted on a workstation to large data structures distributed among data centers. Data structure 146 may also include any combination of one or more data structures controlled by memory controller devices (e.g., server(s), etc.) or software.

Consistent with the present disclosure, communications network 150 may be any type of network (including infrastructure) that supports communications, exchanges information, and/or facilitates the exchange of information between the components of system 100. For example, communications network 150 may include or be part of the Internet, a Local Area Network, wireless network (e.g., a Wi-Fi/302.11 network), or other suitable connections. In other embodiments, one or more components of system 100 may communicate directly through dedicated communication links, such as, for example, a telephone network, an extranet, an intranet, the Internet, satellite communications, off-line communications, wireless communications, transponder communications, a local area network (LAN), a wide area network (WAN), a virtual private network (VPN), or any other mechanism or combinations of mechanism that enable data transmission.

The components and arrangements of system 100 shown in FIG. 1 are intended to be exemplary only and are not intended to limit the disclosed embodiments, as the system components used to implement the disclosed processes and features may vary.

Figure 2:
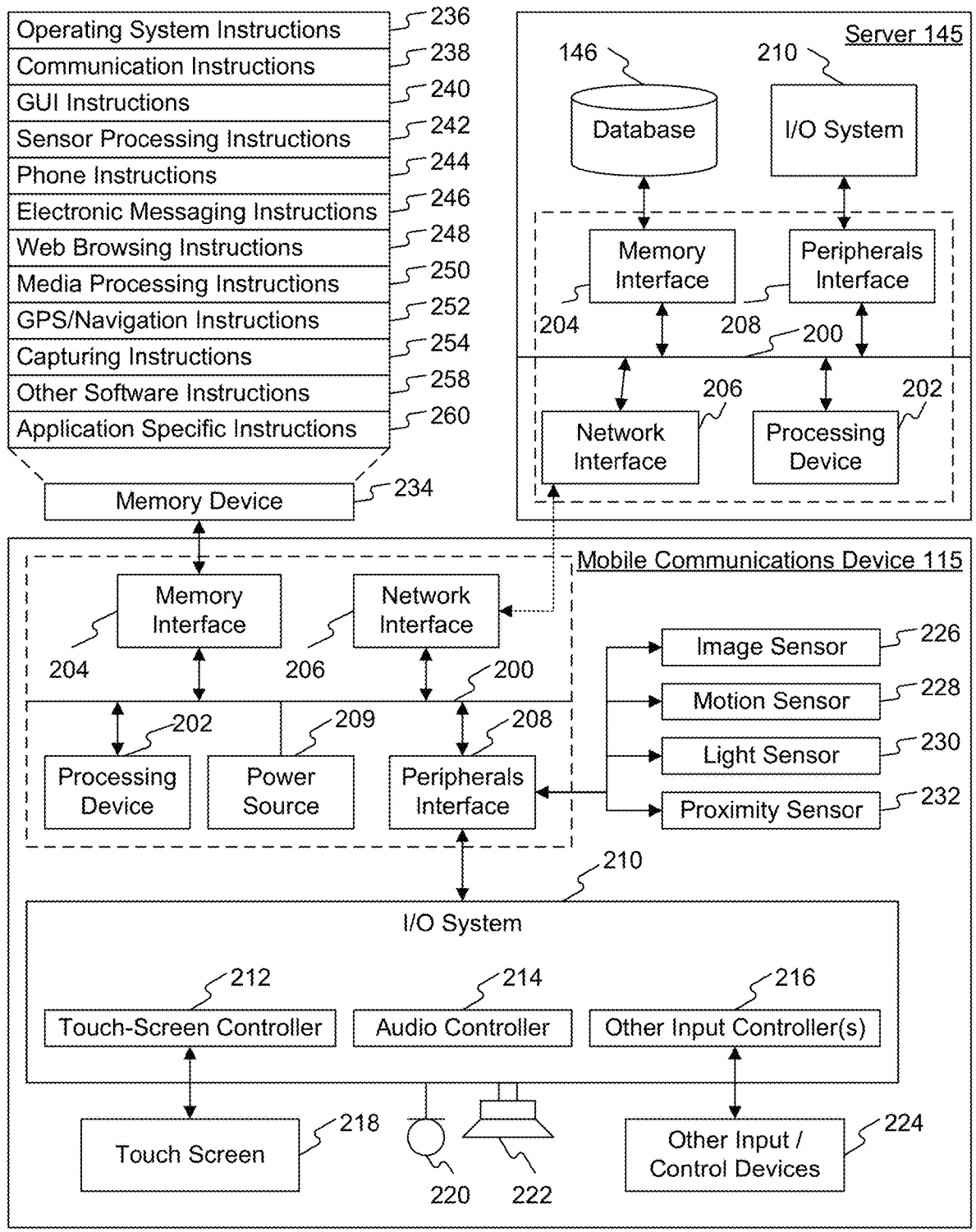
FIG. 2 is a block diagram illustrating some of the components of the system of FIG. 1, consistent with the present disclosure.

FIG. 2 is an exemplary block diagram of configurations of server 145 and mobile communications device 115. In one embodiment, server 145 and mobile communications device 115 directly or indirectly accesses a bus 200 (or other communication mechanism) that interconnects subsystems and components for transferring information within server 145 and/or mobile communications device 115. For example, bus 200 may interconnect a processing device 202, a memory interface 204, a network interface 206, a peripherals interface 208 connected to I/O system 210, and power source 209.

Processing device 202, shown in FIG. 2, may include at least one processor configured to execute computer programs, applications, methods, processes, or other software to perform embodiments described in the present disclosure. For example, the processing device may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing device may include at least one processor configured to perform functions of the disclosed methods such as, for example, a microprocessor manufactured by Intel™. The processing device may include a single core or multiple core processors executing parallel processes simultaneously. In one example, the processing device may be a single core processor configured with virtual processing technologies. The processing device may implement virtual machine technologies or other technologies to provide the ability to execute, control, run, manipulate, store, etc., multiple software processes, applications, programs, etc. In another example, the processing device may include a multiple-core processor arrangement (e.g., dual, quad core, etc.) configured to provide parallel processing functionalities to allow a device associated with the processing device to execute multiple processes simultaneously. It is appreciated that other types of processor arrangements could be implemented to provide the capabilities disclosed herein.

In some embodiments, processing device 202 may use memory interface 204 to access data and a software product stored on a memory device or a non-transitory computer-readable medium. For example, server 145 may use memory interface 204 to access data structure 146. As used herein, a non-transitory computer-readable storage medium refers to any type of physical memory on which information or data readable by at least one processor can be stored. Examples include random access memory (RAM), read-only memory (ROM), volatile memory, nonvolatile memory, hard drives, CD ROMs, DVDs, flash drives, disks, any other optical data storage medium, any physical medium with patterns of holes, a RAM, a PROM, and EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within mobile communications device 115, server 145, or at a remote location. Additionally, one or more computer-readable storage mediums can be utilized in implementing a computer-implemented method. The term "computer-readable storage medium" should be understood to include tangible items and exclude carrier waves and transient signals.

Both mobile communications device 115 and server 145 may include network interface 206 coupled to bus 200. Network interface 206 may provide two-way data communications to a network, such as network 150. In FIG. 2, the wireless communication between mobile communications device 115 and server 145 is represented by a dashed arrow. In one embodiment, network interface 206 may include an integrated services digital network (ISDN) card, cellular modem, satellite modem, or a modem to provide a data communication connection over the Internet. As another example, network interface 206 may include a wireless local area network (WLAN) card. In another embodiment, network interface 206 may include an Ethernet port connected to radio frequency receivers and transmitters and/or optical (e.g., infrared) receivers and transmitters. The specific design and implementation of network interface 206 may depend on the communications network(s) over which mobile communications device 115 and server 145 are intended to operate. For example, in some embodiments, mobile communications device 115 may include network interface 206 designed to operate over a GSM network, a GPRS network, an EDGE network, a Wi-Fi or WiMAX network, and a Bluetooth® network. In any such implementation, network interface 206 may be configured to send and receive electrical, electromagnetic, or optical signals that carry digital data streams representing various types of information.

Both mobile communications device 115 and server 145 may also include peripherals interface 208 coupled to bus 200. Peripherals interface 208 may be connected to sensors, devices, and subsystems to facilitate multiple functionalities. In one embodiment, peripherals interface 208 may be connected to I/O system 210 configured to receive signals or input from devices and to provide signals or output to one or more devices that allow data to be received and/or transmitted by mobile communications device 115 and server 145. In one example, I/O system 210 may include a touch screen controller 212, audio controller 214, and/or other input controller(s) 216. Touch screen controller 212 may be coupled to a touch screen 218. Touch screen 218 and touch screen controller 212 may, for example, detect contact, movement or break thereof using any of a plurality of touch sensitivity technologies, including, but not limited to, capacitive, resistive, infrared, and surface acoustic wave technologies as well as other proximity sensor arrays or other elements for determining one or more points of contact with the touch screen 218. Touch screen 218 may also, for example, be used to implement virtual or soft buttons and/or a keyboard. While a touch screen 218 is shown in FIG. 2, I/O system 210 may include a display screen (e.g., CRT or LCD) in place of touch screen 218. Audio controller 214 may be coupled to a microphone 220 and a speaker 222 to facilitate voice-enabled functions, such as voice recognition, voice replication, digital recording, and telephony functions. The other input controller(s) 216 may be coupled to other input/control devices 224, such as one or more buttons, rocker switches, thumbwheel, infrared port, USB port, and/or a pointer device such as a stylus.

With regard to mobile communications device 115, peripherals interface 208 may also be connected to an image sensor 226, a motion sensor 228, a light sensor 230, and/or a proximity sensor 232 to facilitate image capturing, orientation, lighting, and proximity functions. Other sensors (not shown) may also be connected to the peripherals interface 208, such as a temperature sensor, a biometric sensor, or other sensing devices to facilitate related functionalities. In addition, a GPS receiver may also be integrated with, or connected to, mobile communications device 115, such as GPS receivers typically integrated into mobile communications devices. Alternatively, GPS software may permit a mobile communications device to access an external GPS receiver (e.g., connecting via a serial port or Bluetooth).

Consistent with the present disclosure, mobile communications device 115 may use memory interface 204 to access memory device 234. Memory device 234 may include high-speed random-access memory and/or non-volatile memory such as one or more magnetic disk storage devices, one or more optical storage devices, and/or flash memory (e.g., NAND, NOR). Memory device 234 may store an operating system instructions 236, such as DARWIN, RTXC, LINUX, iOS, UNIX, OSX, WINDOWS, or an embedded operating system such as VxWorks. The operating system 236 may include instructions for handling basic system services and for performing hardware-dependent tasks. In some implementations, the operating system 236 may be a kernel (e.g., UNIX kernel).

Memory device 234 may also store communication instructions 238 to facilitate communicating with one or more additional devices, one or more computers and/or one or more servers. Memory device 234 may include: graphical user interface instructions 240 to facilitate graphic user interface processing; sensor processing instructions 242 to facilitate sensor-related processing and functions; phone instructions 244 to facilitate phone-related processes and functions; electronic messaging instructions 246 to facilitate electronic-messaging related processes and functions; web browsing instructions 248 to facilitate web browsing-related processes and functions; media processing instructions 250 to facilitate media processing-related processes and functions; GPS/navigation instructions 252 to facilitate GPS and navigation-related processes and instructions; capturing instructions 254 to facilitate processes and functions related to image sensor 226; and/or other software instructions 258 to facilitate other processes and functions. Memory device 234 may also include application specific instructions 260 to facilitate a process for guiding user 110 on the steps of the medical testing. For example, application specific instructions 260 may cause display of a massage indicative of image insufficiency for medical testing.

Each of the above identified instructions and applications may correspond to a set of instructions for performing one or more functions described above. These instructions need not be implemented as separate software programs, procedures, or modules. Memory device 234 may include additional instructions or fewer instructions. Furthermore, various functions of mobile communications device 115 may be implemented in hardware and/or in software, including in one or more signal processing and/or application specific integrated circuits. For example, mobile communications device 115 may execute an image processing algorithm to identify the colors and sizes of segments of an examined skin feature in a received image. In addition, the components and arrangements shown in FIG. 2 are not intended to limit the disclosed embodiments. As will be appreciated by a person skilled in the art having the benefit of this disclosure, numerous variations and/or modifications may be made to the depicted configuration of server 145. For example, not all components may be essential for the operation of server 145 in all cases. Any component may be located in any appropriate part of server 145, and the components may be rearranged into a variety of configurations while providing the functionality of the disclosed embodiments. For example, some servers may not include all of the elements in I/O system 210.

Consistent with the present disclosure, system 100 may be used to monitor the visual appearance of skin feature 134. For example, system 100 may provide two-dimensional measurements of different sections of skin feature 134 associated with a same color, such as size and shape characteristics (symmetry, boundary length, etc.). In some embodiments, system 100 may track skin feature parameters over time by repeatedly capturing the same skin feature over time. In this regard, colorized surface 132 may assist in determining variations over time. In one example, skin feature 134 may include scar tissue or a rash that may be monitored daily to track healing progress. In another example, skin feature 134 may be captured weekly or even monthly for monitoring potentially cancerous features or developments. When collecting such data over a period of time, an additional step may be added for verifying that the correction of image 130 is consistent across the time period in which the data was collected. Correcting image 130 may further include taking into account illumination conditions and capturing parameters associated with previously captured images. Additional details on colorized surface 132, which may be used for monitoring the condition of skin feature 134, are described in Applicant's U.S. Pat. No. 10,362,984, which is incorporated herein by reference in its entirety.

Figure 3:
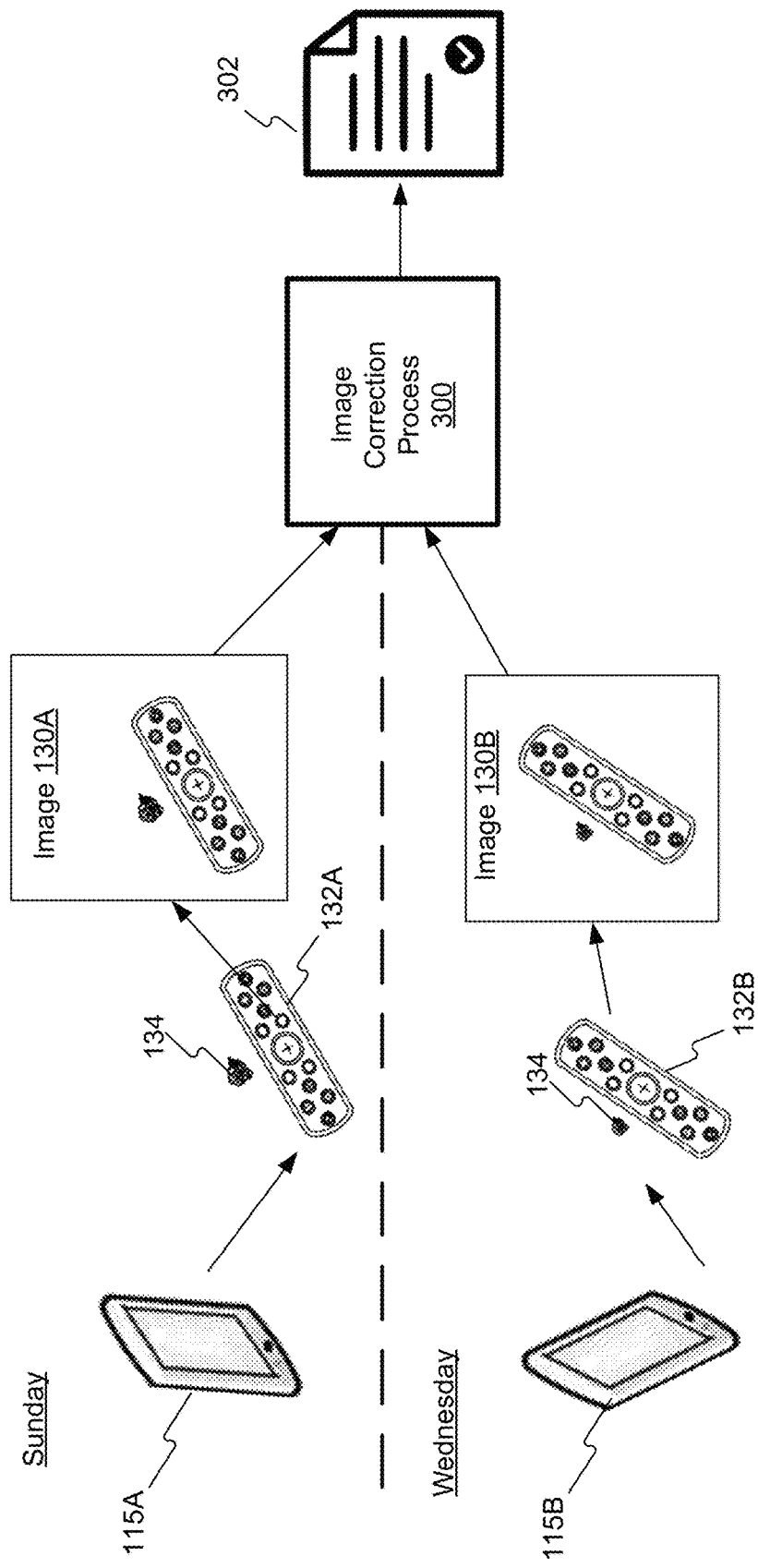
FIG. 3 is a schematic illustration of how the system calibrates the colors of two images captured at different times, consistent with the present disclosure.

As mentioned above, one of the challenges of turning a smartphone into a regulatory-approved clinical device is the lack of uniformity of image capture capabilities of smartphones. FIG. 3 illustrates the general case of two communication devices 115 capturing the same skin feature at different times. In the illustrated example, on Sunday, when a first mobile communications device 115A captures skin feature 134 in proximity to a first colorized surface 132A, a first image 130A is acquired; and on Wednesday, when a second mobile communications device 115B captures skin feature 134 in proximity to a second colorized surface 132B, a second image 130B is acquired. Other than the illustrated differences between first image 130A and second image 130B (i.e., skin feature 134 had shrunken and the colorized surfaces have different orientations), first image 130A may vary from second image 130B due to differences between the incorporated image sensors, differences in lighting conditions from light sources, differences in image sensor settings, and more. For example, first image 130A may be different from second image 130B because first mobile communications device 115A has different white balance settings and different color correction profiles than second mobile communications device 115B. The white balance settings may be associated with how each of the communication devices determines the white point for the image and if any tint should be applied to the other colors. The color correction profile may be associated with how communication devices 115 process color saturation, black levels, highlights, and the contrast of colors in the image. In another example, first image 130A may be different from second image 130B because first mobile communications device 115A has different hardware (such as image sensor resolution, dimensions, filters, color filters, lenses, crop factor, sensitivity, and so forth). In yet another example, first image 130A may be different from second image 130B because first mobile communications device 115A has different camera configuration (such as exposure time, shutter speed, aperture, ISO, and so forth).

Consistent with the present disclosure, each of image 130A and image 130B may undergo an image correction process 300. Image correction process 300 may include one or more steps to remove (or to compensate for) local illumination effects and image capturing settings effects. The local illumination effects may result from the type of light source used to light the skin feature, the distance of the skin feature from the light source, a viewing angle of the skin feature, position of the skin feature, ambient light conditions, flash usage, exposure time, and so forth. The image capturing settings effects may result from the type of image sensor 226 used to capture the skin feature, image resolution, frame rate, gain, ISO, shutter speed, stereo base, lens, focus, zoom, color correction profile, and so forth. In some embodiments of the disclosure, correcting captured image 130 may include reversing any of the tone mapping, color enhancement, white balance, and contrast enhancing of image 130. In addition, correcting image 130 may include simulating standard illumination conditions and reducing shading and specular effects. A person skilled in the art would recognize that even if images 130A and 130B were captured by a same communication device 115, image correction process 300 may still need to take place in order to remove undesired effects and to accurately determine the condition of skin feature 134.

In one embodiment, image correction process 300 may be enabled through the use of colorized surface 132. Specifically, the qualities of the one or more color patches on colorized surface 132 may be known in advance. To the extent differences are detected between the colors of colorized surface 132A and the colors of colorized surface 132B, the system may calculate a correction factor for rectifying such differences, and then apply that correction factor to the colors of skin feature 134.

Image correction process 300 may correct each of first image 130A and second image 130B, correct only one of the images, correct only selected areas of first image 130A, or correct only selected areas of second image 130B. For example, image correction process 300 may include increasing the red color in first image 130A and adding brightness to second image 130B. After images 130A and 130B undergo image correction process 300, system 100 may determine results 302 from the changes between first image 130A and second image 130B. In accordance with the present disclosure, image correction process 300 ensures that results 302 reflect only the visual changes of skin feature 134 that occurred naturally over time and devoid of visual changes of skin feature 134 that occurred artificially due to different illumination effects and capturing effects. In one embodiment, image correction process 300 can ensure the reliability of results 302 because both images captured the same type of colorized surface 132 whose colorization is known in advance, and which may be used as a basis for generating different correction factors for the varying differences. In some embodiments, system 100 may correct first image 130A and/or second image 130B using metadata associated with the mobile communications device that captured the image. In other embodiments, system 100 may correct captured image 130 without using any information about the mobile communications device that captured image 130. In one example, system 100 may calculate one or more convolutions of pixels of first image 130A and/or of second image 130B, and may use the calculated one or more convolutions of the pixels to correct first image 130A and/or second image 130B respectively. In one example, a machine learning model may be trained using training examples to remove local illumination effects from images, and system 100 may use the trained machine learning model to correct first image 130A and/or second image 130B. An example of a training example may include a pair of example images, including a first example image of a scene with varying illumination conditions, and a second example image of the same scene with desired illumination conditions and/or after removal of the local illumination effects from the first example image.

Consistent with the present disclosure, system 100 may use results 302 to monitor the visual appearance of skin feature 134 over time. For example, system 100 may identify skin feature parameters in each of the images. The skin feature parameters may include: two dimensional measurements of different segments of skin feature 134 associated with a same color, such as size and shape characteristics (symmetry, boundary length, etc.). Thereafter, system 100 may track the changes of the skin feature parameters over time. In one example, skin feature 134 may include scar tissue or a rash that may be monitored daily to track healing progress. In another example, skin feature 134 may be captured weekly or even monthly for monitoring potentially cancerous features or developments. When collecting such data over a period of time, an additional step may be added for verifying that the correction of the captured images is consistent across the time period in which the data was collected. Correcting second image 130B may further include taking into account illumination conditions and capturing parameters associated with first image 130A. Additional details on techniques and algorithms included in image correction process 300 which may be used for correcting the colors of skin feature 134 are described in Applicant's U.S. Pat. No. 10,362,984, which is incorporated herein by reference in its entirety.

Figure 4:
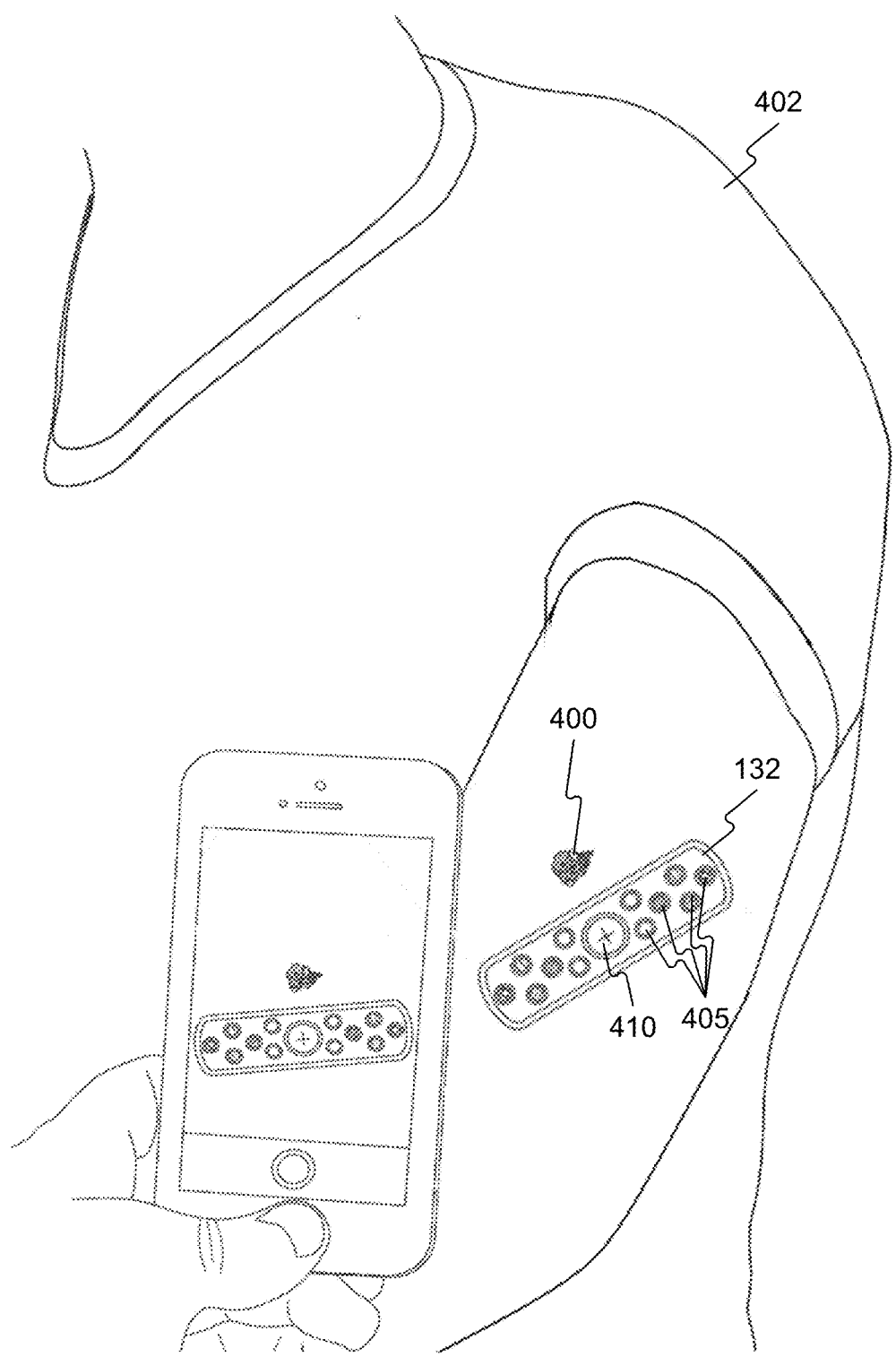
FIG. 4 is a schematic illustration of using a smartphone to examine a wound, consistent with the present disclosure.

FIG. 4 depicts one exemplary embodiment where skin feature 134 is a wound 400 that patient 402 may have. In this embodiment, system 100 is configured to measure the distribution of colors of wound 400 by comparing them to the colors on colorized surface 132. The colors on colorized surface 132 may be selected to include an at least some of the expected range of colors of the examined skin feature under various illumination and capturing conditions. It may also include a range of colors from which a correction factor may be generated. As illustrated in FIG. 4, colorized surface 132 may include a plurality of colored reference elements 405 and may be attachable onto a skin area next to wound 400. In certain embodiments, colorized surface 132 may have different forms adapted to a medical condition of patient 402, the specific skin tone of patient 402, or an expected form and characteristics of wound 400. In addition, colorized surface 132 may have different forms adapted to the expected capturing parameters (e.g., to capturing geometry). For example, colorized surface 132 may be round, elongated, curved, have one or more openings therein to accommodate wound 400, etc.

Consistent with the present disclosure, colorized surface 132 may have one or more colored reference elements 405 used for calibrating illumination and capturing conditions rather than or in addition to relating to colored reference elements 405 associated with the expected colors in wound 400. When wound 400 and colorized surface 132 are captured in a single image, system 100 may determine the true colors of captured wound 400 by correcting image 130 using image correction process 300 described above. For example, medical analysis unit 140 may compute the color constancy of wound 400 to determine whether two pixels have the same color in the real world, regardless of illumination conditions and/or camera parameters. In some embodiments, colorized surface 132 may also include one or more positioning marks 410 that may be used for image processing purposes and/or for positioning colorized surface 132 (and for positioning other elements of colorized surface 132, such as colored reference elements 405) accurately with respect to wound 400. Moreover, positioning marks 410 may provide a reference of a known dimension that may be used to estimate a size, orientation, and/or a form of wound 400. In certain embodiments, positioning marks 410 of colorized surface 132 may be used (e.g., by medical analysis unit 140) to correct captured image 130 with respect to its dimensions and forms and to derive an analysis of size and/or form of wound 400 and possibly of other skin features.

Figure 5:
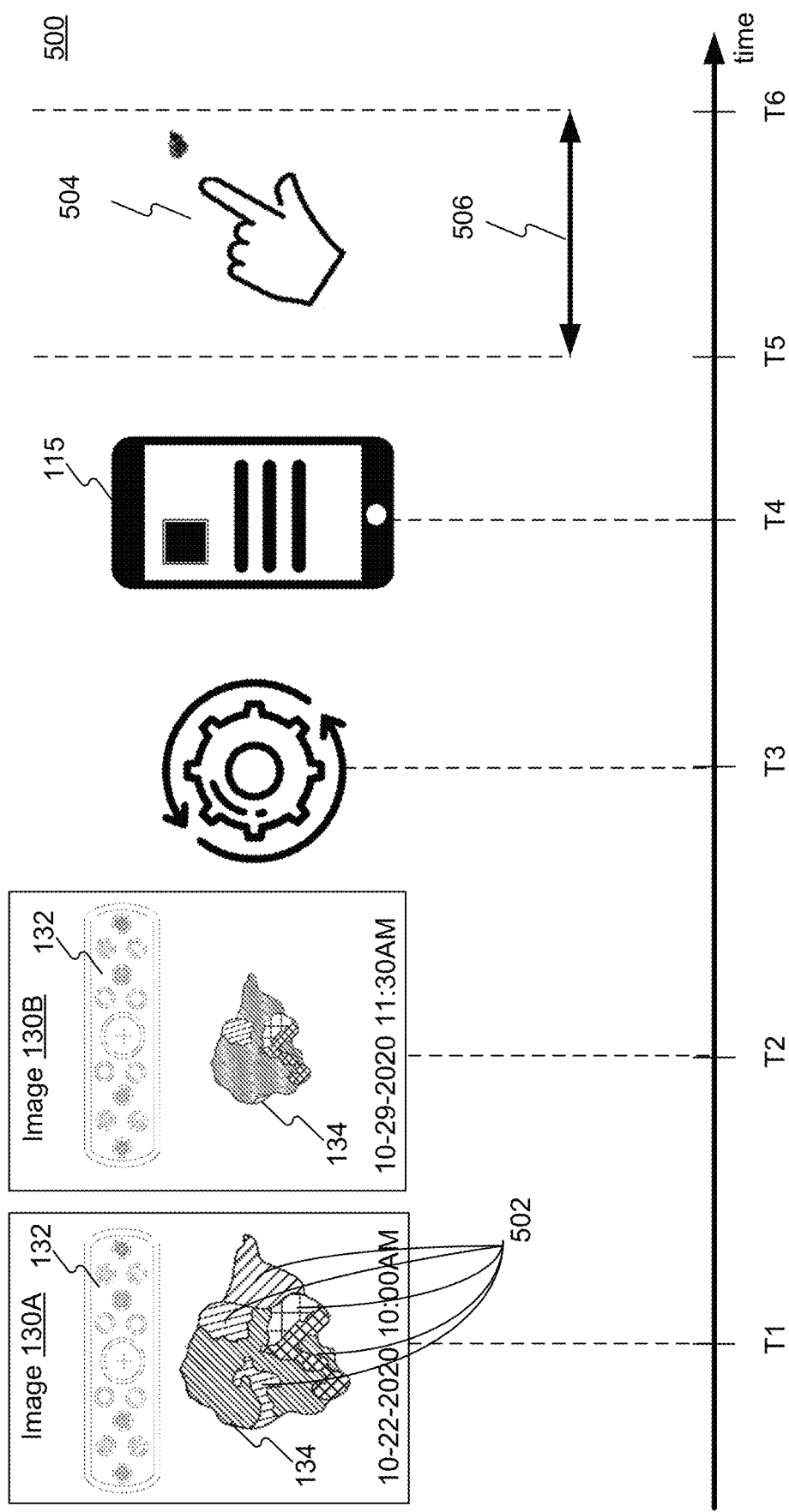
FIG. 5 is a schematic diagram showing an example timeline illustrating how the system of FIG. 1 may be used for monitoring and treating a skin feature using image processing, consistent with the present disclosure.

FIG. 5 is a diagram showing an example timeline 500 illustrating how system 100 may be used for monitoring and treating skin feature 134 using image processing. The manner and order in which events are shown in timeline 500 is chosen for convenience and clarity of presentation and is not intended to limit the disclosed embodiments. Instead, the proper chronological relationship between events shown in timeline 500 depends on the application and is defined by the appended claims. In particular, the time difference between two consecutive events in timeline 500 may be a short time interval of only a few moments or be a relative long-time interval of several hours and even days. Moreover, timeline 500 illustrates only two incidences where images of skin feature 134 are captured and processed by medical analysis unit 140; however, a person skilled in the art would recognize that more images than two may be captured and process during a long period of time.

Consistent with the present disclosure, first image 130A may be captured at time T1 and second image 130B may be captured at time T2. In the illustrated example, the time difference between T1 and T2 is about a week, yet in other cases the time difference between T1 and T2 may be more than an hour and less than a day, more than a day and less than a month, more than two days, more than four days, more than a week and less than a year, more than a month, more than six months, more than a year. In addition, although first image 130A may be captured at different times both images may be received by medical analysis unit 140 at the same time, e.g., subsequent to T2. In some embodiments, second image 130B may be captured at least a day after first image 130A is captured. For example, first image 130A may be captured at the outset of a medical treatment to skin feature 134 and second image 130B may be captured at least a day after applying the medical treatment to skin feature 134.

At time T3, medical analysis unit 140 may analyze data associated with first image 130A and second image 130B to determine a condition of skin feature 134. Additionally or alternatively, medical analysis unit 140 may analyze data associated with first image 130A at a time between T1 and T2. Consistent with the present disclosure, skin feature 134 may have multiple segments 502 of differing colors and differing sizes and the determination of the condition of skin feature 134 may be based on changes over time of segments 502. Specifically, each image may be stored and analyzed individually to determine image data associated with the captured images. The image data may include values of various parameters such as distribution of colors of segments 502, one or more geometric parameters (e.g., form, border, symmetry, two- or three-dimensional form), dimensions (e.g., size or height), and more. In one embodiment, medical analysis unit 140 may be configured to determine values of any of the above-mentioned parameters and their combinations from the first and second images. In an alternative embodiment, the values of any of the above-mentioned parameters and their combinations may be determined by mobile communication device 115. Thereafter, medical analysis unit 140 may analyze the image data (e.g., the images themselves or the values of any of the above-mentioned parameters) to track changes in distribution of colors of segments 502 and/or the rate of changes of any skin feature parameters over time, by comparing the image data associated with first image 130A and the image data associated with second image 130B. In the illustrated example, the changes of the multiple segments of skin feature 134 between first image 130A and second image 130B can be seen by naked eyes; however, in many cases the changes may be so subtle that only a trained neural network configured to identify the segments of skin features may be able to detect changes. In one embodiment, when first image 130A is captured at the outset of a medical treatment and second image 130B is captured at least a day after applying the medical treatment, medical analysis unit 140 may also calculate the level of effectiveness of the medical treatment to determine if it is above or below a threshold.

Consistent with the present disclosure, medical analysis unit 140 may determine, based on the condition of skin feature 134, at least one medical action 504 for monitoring or treating the skin feature. The determined medical action may be intended to increase effectiveness of the medical treatment (e.g., applying a medicine to the skin feature over a treatment period) or to monitor the condition of the skin feature (e.g., determining a time for examining the skin feature by the medical professional). In some embodiments, medical analysis unit 140 may determine when medical action 504 needs to take place. Specifically, medical analysis unit 140 may determine time T5 for a starting medical action 504 and/or time T6 for completing medical action 504. The determined times T5 and T6 define a time period 506 for completing medical action 504. In a first example, medical analysis unit 140 may determine that a medical procedure of removing dead or inflamed tissue is needed ASAP. In a second example, medical analysis unit 140 may determine that an ultrasound and electromagnetic therapy within a month from T2 may assist the healing progress of skin feature 134. In a third example, medical analysis unit 140 may determine that biopsy of skin feature 134 is needed in the next two to three months. In a fourth example, medical analysis unit 140 may determine that a visual examination of skin feature 134 by a medical practitioner is needed at a time between nine months to a year. In a fifth example, medical analysis unit 140 may determine that capturing a third image of skin feature 134 is needed at least one day after second image 130B was captured but no later than three days after second image 130B was captured. Additionally or alternatively, medical analysis unit 140 may determine time between T5 and T6 for a medical action 504, and a user may select T5 and/or T6 according to the determined time.

At time T4, information indicative of medical action 504 and possibly information indicative of time period 506 for completing the medical action 504 may be provided to user 110 (or medical practitioner 120). The information may be provided visually, textually, audibly, through an external device, through a calendar event, through a scheduling system, to an external device, to a scheduling system, and so forth. In some embodiments, medical analysis unit 140 may cause mobile communications device 115 (or mobile communications device 125) to display the determined information. One example of causing the mobile communications device to display the information indicative of medical action 504 may include sending a notification to user 110 (or medical practitioner 120), the notification may include a link for opening an application for capturing a third image of skin feature 134. The notification may be issued at a time associated with time period 506, for example, at a predetermined time before time period 506 starts, at time T5 which is the beginning of time period 506, at a predetermined time before time period 506 ends, and so forth. In another example, a notification for reminding user 110 (or medical practitioner 120) to complete medical action 504 may be provided. For example, the notification may be provided visually, textually, audibly, through an external device, to an external device, and so forth.

Figure 6:
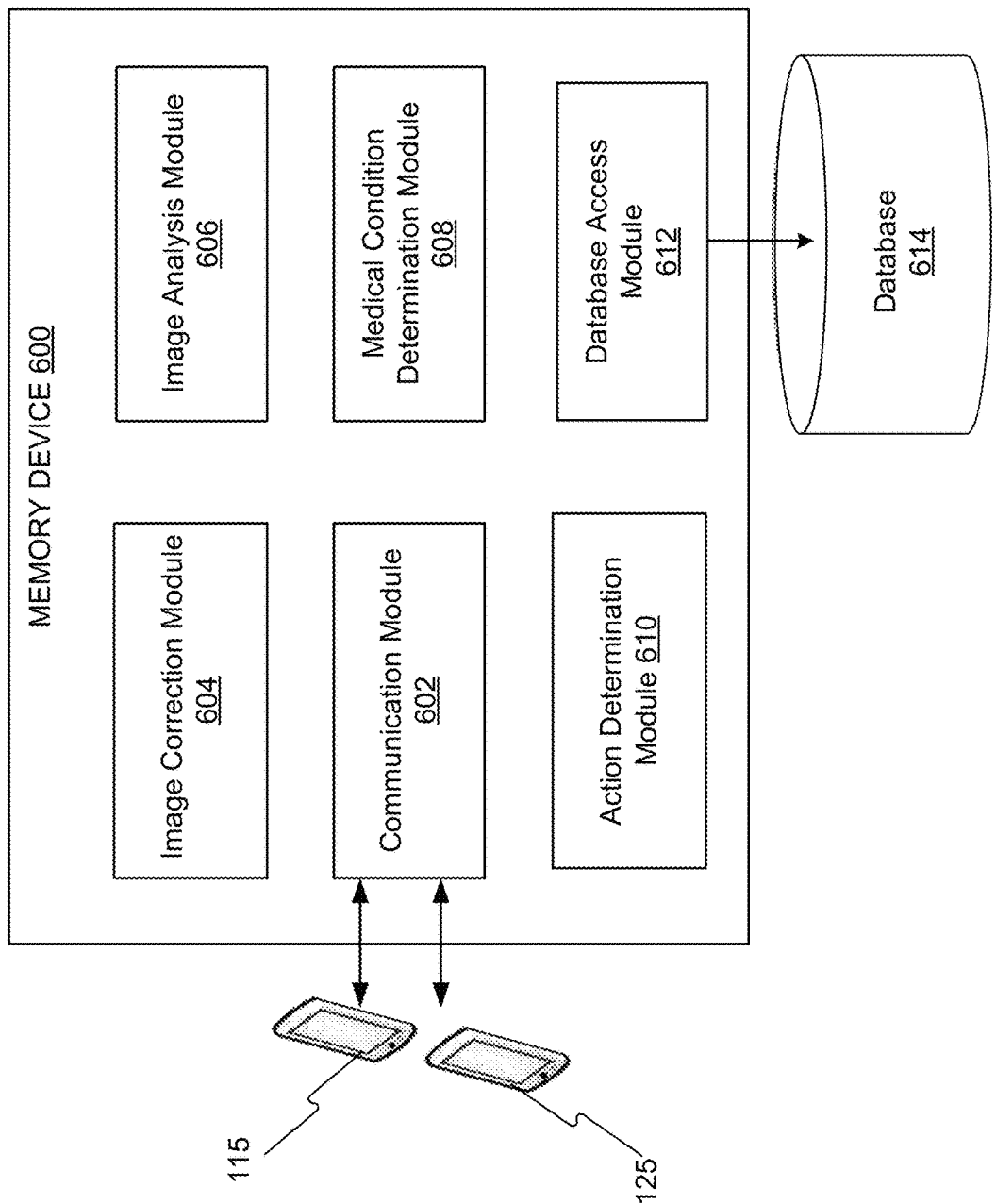
FIG. 6 is a block diagram of software modules configured to perform one or more operations, consistent with the disclosed embodiments.

FIG. 6 is a block diagram of software modules configured to perform one or more operations, consistent with the disclosed embodiments. In particular, as shown, a memory device 600 may include a communication module 602, an image correction module 604, an image analysis module 606, a medical condition determination module 608, an action determination module 610, a database access module 612, and a database 614. Modules 602, 604, 606, 608, 610, and 612 may contain software instructions for execution by at least one processor (e.g., processing device 202) associated with system 100. Communication module 602, image correction module 604, image analysis module 606, medical condition determination module 608, action determination module 610, database access module 612, and database 614 may cooperate to perform multiple operations. For example, communication module 602 may receive multiple images of a skin feature from a mobile communications device of user 110, image correction module 604 may correct the received images by removing one or more local illumination variations effects and image capturing process effects to depict calibrated colors of the skin feature, image analysis module 606 may identify the changes in the colors and sizes of segments of the examined skin feature in the received images, medical condition determination module 608 may determine the condition of the examined skin feature, and action determination module 610 may determine an action for treating the skin feature (e.g., medical action 504) and in some cases a time period for completing the medical action (time period 506).

In some embodiments, memory device 600 may be part of system 100, for example, data structure 146. Alternatively, memory device 600 may be stored in an external database or an external storage communicatively coupled with server 145, such as one or more databases or memories accessible over communication network 150. Further, in other embodiments, the components of memory device 600 may be distributed in more than one computing device, for example, server 145 and communication device 115. Specifically, in the illustrated configuration, data structure 146 of server 145 may include communication module 602 and image correction module 604 that include instructions to receive images from user 110 and to rectify the images using image correction algorithms. But in other configurations, memory device 234 of communication device 115 may include image correction module 604 for locally rectifying captured images, and communication module 602 that resides in data structure 146 of server 145 may receive the already-rectified images.

In some embodiments, communication module 602 may receive multiple images of a skin feature from mobile communications device 115 or mobile communications device 125 and may cause a mobile communications device to display information indicative of the action determined by action determination module 610. Consistent with the present disclosure, communication module 602 may include software instructions for facilitating communications between the device on which it is implemented (e.g., server 145) and another component of system 100 (e.g., mobile communications device 115, mobile communications device 125, and any other communication device of healthcare provider 160, insurance company 170, and pharmacy 180). Communication module 602 may enable receipt and transmission of data from and to user 110. For example, the received data may include two or more images, and lifestyle information of user 110. The transmitted data may be associated with actions associated with the condition of the skin feature.

In some embodiments, image correction module 604 may remove local illumination variations effects and image capturing effects from the images received by communication module 602. Consistent with the present disclosure, image correction module 604 may include software instructions for using the colored reference set of colorized surface 132 depicted in the received images to identify local illumination conditions and image capturing settings. Thereafter, image correction module 604 may use image correction algorithms (e.g., image correction process 300) to rectify the first and second images to enable determining the colors of the skin feature, irrespective of local illumination conditions and irrespective of image capturing settings. With reference to the embodiment illustrated in FIG. 3, when correcting first image 130A, image correction module 604 may determine chromatic properties of the colored reference set of colorized surface 132A, by directly analyzing first image 130A itself, and/or by examining data containing chromatic property information of colorized surface 132A. This data may be included within metadata of the image or may be accessed by reading a machine-readable code (e.g., a scannable code attached to colorized surface 132A). Based on the determined local illumination conditions, chromatic properties, and/or based on the image capturing parameters, image correction module 604 may correct the image. Image correction may physically alter an image, or it may simply occur through calculations without a physical alteration of the image. Some disclosed embodiments may include using the colored reference elements to determine the local illumination conditions and separately rectifying colors of the multiple segments of the skin feature based on the local illumination conditions. For example, if the light quality causes a specific misperception of the known color reference elements, then the correction necessary for the color reference elements may be applied to a skin feature, thereby correcting a color of at least one segment of the skin feature. Some examples of techniques for such correction of the image are described above.

In some embodiments, image analysis module 606 may identify the changes of the examined skin feature in the images corrected by image correction module 604. Consistent with the present disclosure, image analysis module 606 may include software instructions for conducting edge identification, in which an image is analyzed to detect pixels at which discontinuities (e.g., sudden changes in color) occur, and edges (e.g., edges of segments of a skin feature) are identified to coincide with the detected pixels. Alternatively or additionally, in some embodiments analyzing the corrected images may involve identifying in and/or extracting from an image pixels representative of one or more segments of the skin feature. Pixels may be determined to be representative of segments of the skin feature based on other images of the skin feature maintained in a database and/or predetermined data describing the skin feature. Alternatively or additionally, pixels may be determined to be representative of segments of the skin feature based on a trained neural network configured to detect segments of the skin feature. Other types of analysis are possible as well, including, but not limited to, gradient matching, greyscale matching, scale-invariant feature transform (SIFT) matching, and/or interpretation trees. Image analysis module 606 may determine changes (e.g., changes in color, changes in size, changes in shape, etc.) of the segments of the skin feature between the several corrected images, e.g., between first image 130A and second image 1308.

In some embodiments, medical condition determination module 608 may determine the condition of the examined skin feature based on the changes identified by image analysis module 606. Consistent with the present disclosure, medical condition determination module 608 may include software instructions for determining the condition of the examined skin feature based on a change in appearance of the skin feature between two or more images. For example, medical condition determination module 608 may identify that a combination of color, dimensions, shape, etc., has changed with respect to the skin feature. These changes may be associated with a particular condition of the examined skin feature. For example, medical condition determination module 608 may determine that a size of the skin feature has shrunk and/or that a hue, value, and/or intensity of a color of at least a segment of the skin feature has changed. Based on that changes, medical condition determination module 608 may determine a current condition and/or a predicted condition of the skin feature. In some examples, a machine learning model may be trained using training examples to determine the condition of the skin feature from pairs of images of a skin feature, and the machine learning model may be used to analyze the depiction of the skin feature in the first image and the depiction of the skin feature in the second image to determine the condition of the skin feature. In some examples, a machine learning model may be trained using training examples to determine conditions of skin features from sets of image-related information records, and the trained machine learning model may be used to analyze image-related information based on the first image (such as image 130A) and image-related information based on the second image (such as image 130B) determine the condition of the skin feature. Such training examples may include a set of three of image-related information records, a pair of images as an input and a third image captured sometime after the pair of images to show the progress of the skin feature. The training examples may also include labels indicating the condition of the skin feature, a portion of an image, color information associated with an image, and/or any other data capable of training a machine to determine the condition of a skin feature.

In some embodiments, action determination module 610 may determine an action for associated with the condition of the skin feature and use communication module 602 to cause mobile communications device 115 or mobile communications device 125 to display information indicative of the determined action. Consistent with the present disclosure, action determination module 610 may include software instructions for scheduling an appointment with a medical practitioner of user 110, generating a prescription to user 110, providing an indication that user 110 may be eligible for a different insurance coverage, and more. In one embodiment, action determination module 610 may determine an action for treating the skin feature and determine a time period for completing the action. In another embodiment, the at least one medical action includes monitoring the state of the skin feature by capturing a third image of the skin feature at least one day after the second image was captured. In another embodiment, the at least one medical action includes altering a medical treatment.

In some embodiments, database access module 612 may cooperate with database 614 to retrieve stored reference data such as an electronic medical record (EMR) of user 110 and medical data associated with the type of skin feature 134. Medical condition determination module 608 may use the reference data stored in database 614 to determine the condition of the skin feature. Database 614 may include separate databases, including, for example, a vector database, raster database, tile database, viewport database, and/or a user input database, configured to store data. The data stored in database 614 may be received from modules 602-612, server 145, or from any communication device associated with system 100. Moreover, the data stored in database 614 may be provided as input using data entry, data transfer, or data uploading.

Modules 602-612 may be implemented in software, hardware, firmware, a mix of any of those, or the like. For example, if the modules are implemented in software, the modules may be stored in a server (e.g., server 145) or distributed over a plurality of servers. In some embodiments, any one or more of modules 602-612 and data associated with database 614 may be stored in data structure 146 and/or located on server 145, which may include one or more processing devices. Processing devices of server 145 may be configured to execute the instructions of modules 602-612. In some embodiments, aspects of modules 602-612 may include software, hardware, or firmware instructions (or a combination thereof) executable by one or more processors, alone, or in various combinations with each other. For example, modules 602-612 may be configured to interact with each other and/or other modules of server 145 to perform functions consistent with disclosed embodiments.

Figure 7:
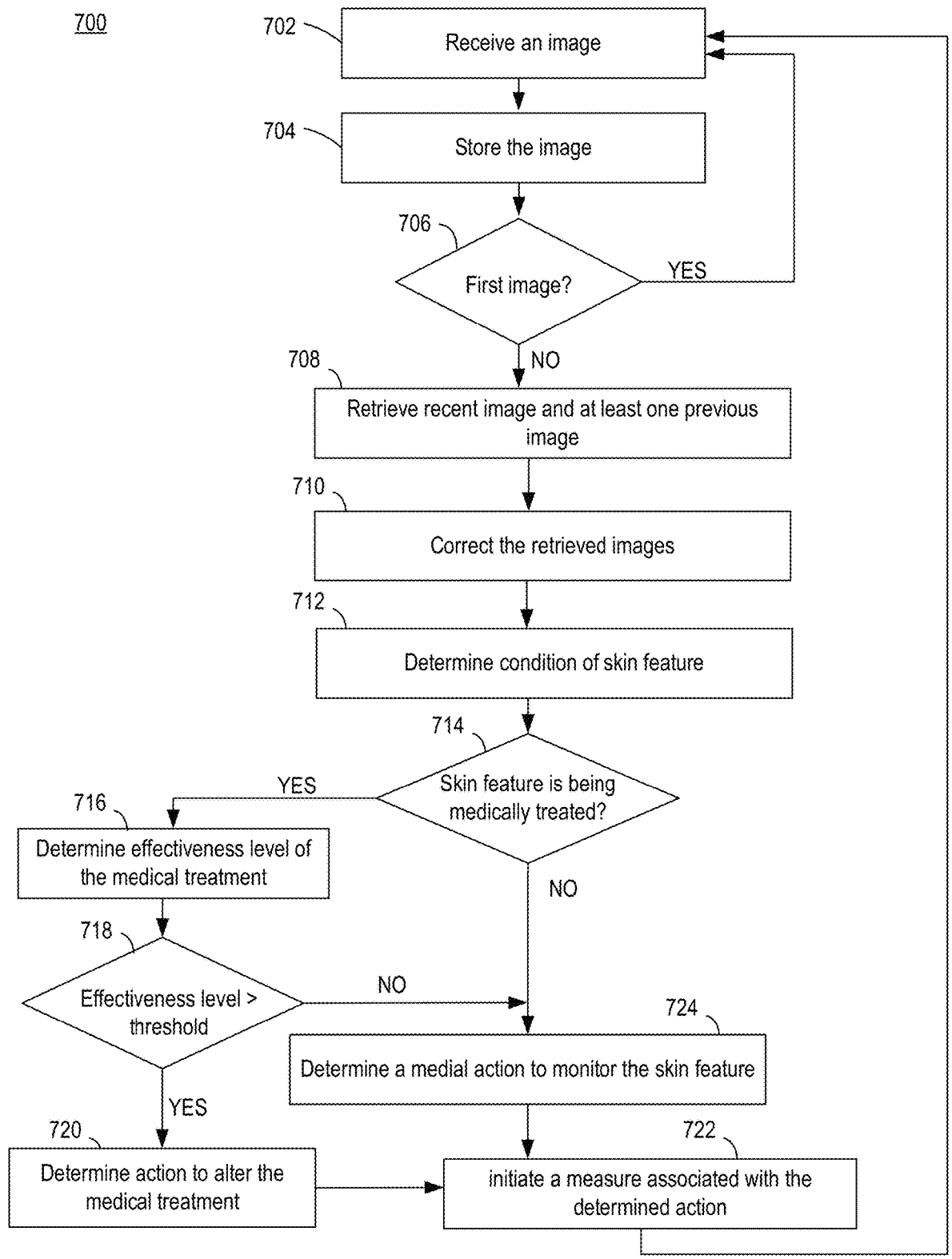
FIG. 7 is a flow chart illustrating an example process for monitoring and treating a skin feature using image processing, consistent with the present disclosure.

FIG. 7 depicts a flowchart of an example process 700 executed by a processing device of system 100 (e.g., processing device 202) for conducting image processing of skin features. Process 700 begins when the processing device receives from at least one image sensor (e.g., image sensor 226) associated with a mobile communications device (e.g., mobile communications device 115) an image of the skin feature (step 702). Thereafter, the processing device may store in at least one memory (e.g., memory device 234 or data structure 146) data associated with the image for later processing (step 704). Thereafter, the processing device determines if the received image is the first image of the skin feature (decision step 706). When the received image is indeed the first image, process 700 repeats steps 702 and 704 to receive a second image. The time duration between the receipt of the first image and the receipt of the second image may depend on the application and may be longer than a day, longer than a week, longer than a month, and so forth. When the received image is the second image or any subsequent image, the processing device may retrieve the most recent image and at least one previous image (step 708). In one embodiment, the processing device may retrieve only two images to determine the condition of the skin feature. In another embodiment, the processing device may retrieve more than two images to determine the condition of the skin feature. Then, the processing device may correct the retrieved images (step 710) to remove local illumination effects, image capturing settings effects, or a combination thereof (e.g., using image correction process 300). Thereafter, the processing device may analyze the corrected images to determine the condition of the skin feature (step 712).

Process 700 may be utilized according to two aspects of the disclosure. In the first aspect of the disclosure, the processing device may determine, based on the condition of the skin feature, an action for monitoring or treating the skin feature and a time period for completing the action. In the second aspect of the disclosure, the processing device may determine, based on the condition of the skin feature, an action to alter a medical treatment determined to be ineffective. Accordingly, process 700 includes determining if the skin feature is being medically treated (decision step 714). The determination whether skin feature is undergoing any medical treatment may be based on information manually provided from user 110 or from medical practitioner 120. Alternatively, the determination whether the skin feature is being medically treated may be based on information retrieved by the processing device from the user's electronic medical record (EMR). In some embodiments, the first image may be captured at the outset of a medical treatment and the second image may be captured at least a day after applying the medical treatment to the skin feature.

In case the processing device determined that the skin feature is being medically treated, process 700 may include determining the effectiveness level of the medical treatment (step 716). As discussed in great detail below, a machine learning model may be trained using training examples to determine the effectiveness level of the medical treatment. Thereafter, the processing device may determine if the level of effectiveness of the medical treatment is below a threshold (decision step 718). When the processing device determines that the level of effectiveness of the medical treatment is below a threshold, process 700 may include determining an action to alter the medical treatment (step 720). The determined action to alter the medical treatment may be based on the condition of the skin feature and the level of effectiveness of the medical treatment. Then, the processing device may initiate a measure associated with the determined action (step 722).

In some embodiments, (e.g., in case the processing device determines that the skin feature is not being medically treated, in case the processing device determines that the skin feature is being medically treated but the effectiveness level of the medical treatment is above the threshold, in case it is requested by a user, and so forth), process 700 may include determining a medical action to monitor the skin feature (step 724). In some embodiments, the determination of the medical action may be based on the condition of the skin feature determined in step 712. Additionally, the determination of the medical action may include a determination of a time period for completing the medical action. For example, the determined medical action may include capturing a third image of the skin feature within a time window of twelve hours starting two days after the second image was captured. Process 700 continues when the processing device initiates a measure associated with the determined action (step 722). In one embodiment, initiating the measure may include causing a display of information indicative of the determined action. Examples of display of information indicative of the determined action are illustrated below with reference to FIGS. 8A and 8B.

Figure 8A:
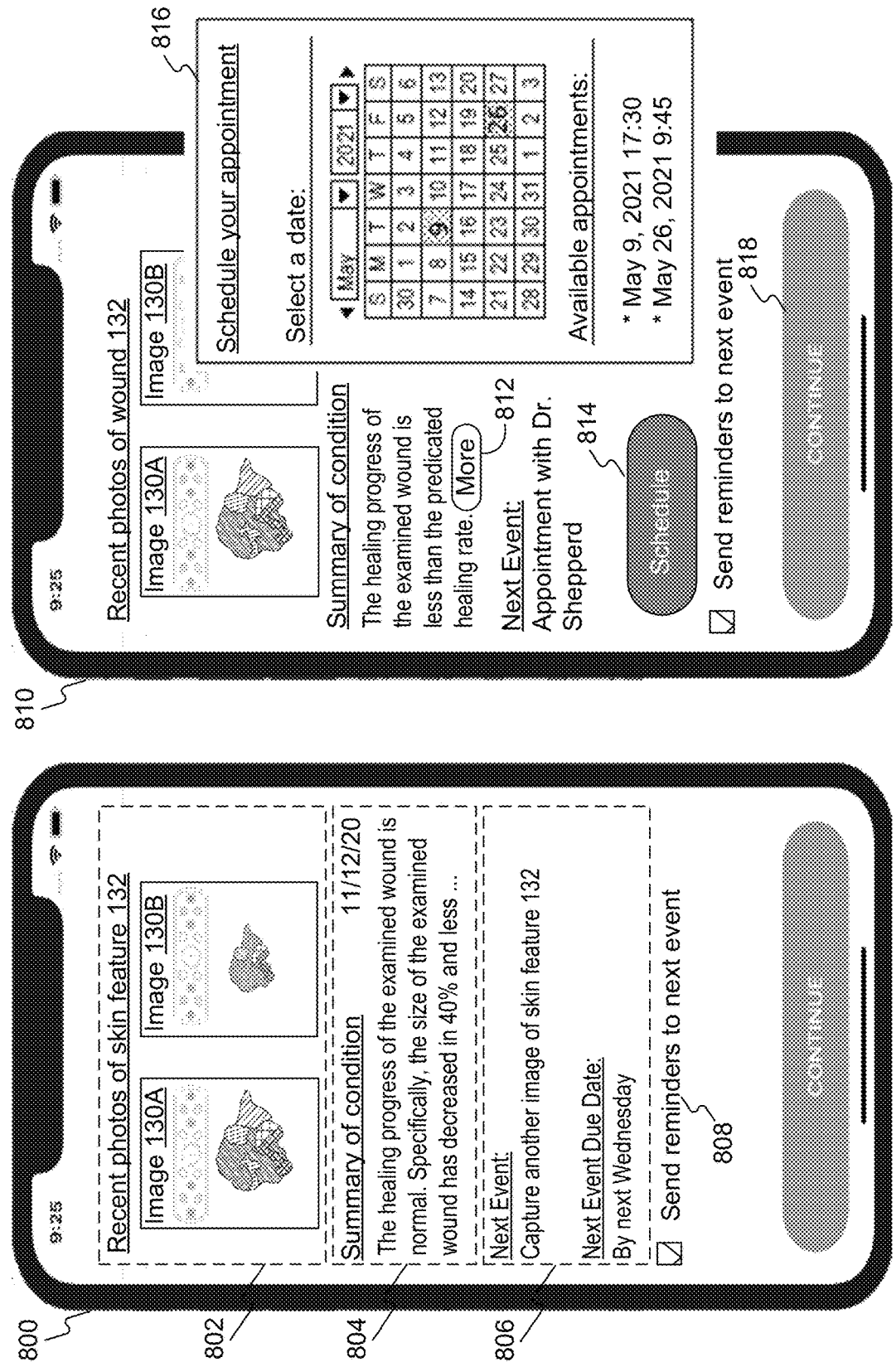
FIG. 8A shows screenshots illustrating an example graphical user interface (GUI) for displaying information indicative of determined medical action, consistent with the disclosed embodiments.
Figure 8B:
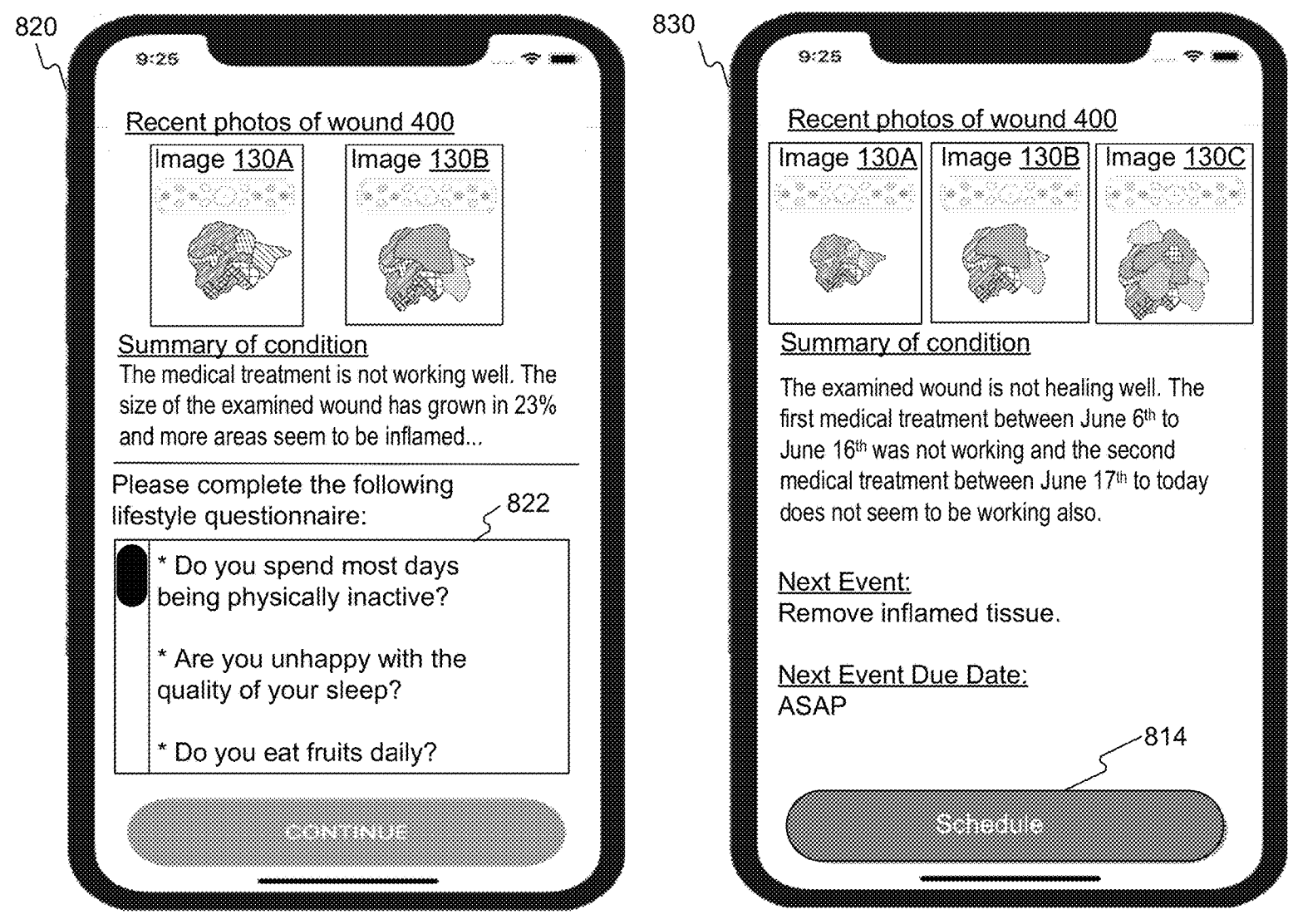

FIGS. 8A and 8B depict four screenshots illustrating a graphical user interface (GUI) for displaying user 110 or medical practitioner 120 information associated with the condition of the skin feature. The screenshots are associated with a non-limiting example of an interactive application and may be displayed on mobile communications device 115 or mobile communications device 125. The screenshots of FIG. 8A are associated with the first aspect of the disclosure and depict information indicative of the medical action determined based on condition of skin feature 134 and information indicative of the time period to complete the medical action. The screenshots of FIG. 8B are associated with the second aspect of the disclosure and depict information indicating that altering an ongoing medical treatment is needed due to the condition of the wound.

In the example depicted in first screenshot 800, the interactive application recommends user 110 to continue monitoring the condition of skin feature 134 by uploading another image of the skin feature to server 145 within a seven-day time window. Specifically, as shown in the figure, the GUI of the interactive application may include a first area 802 displaying representations of images that were used in analyzing skin feature 134. For example, the representations of images 130A and 130B may include thumbnails, timestamps, file names, and more. The GUI of the interactive application may further include a second area 804 displaying a summary of the condition of skin feature 134. In one embodiment, the summary of the condition of skin feature 134 may be generated by processing device 202 using a recurrent neural network (RNN) and hierarchical hidden Markov model. The processing may determine keywords and value of parameters from the determined condition of the skin feature and may generate a written summary using deep learning algorithms and determined keywords. The GUI of the interactive application may further include a third area 806 displaying information indicative of the determined medical action (e.g., the next event) and the determined time period to complete the medical action (e.g., next event due date). In addition, the interactive application may include an option for sending reminders to user 110 on the next event.

In the example depicted in second screenshot 810, the interactive application recommends user 110 to visit his or her medical practitioner and access a scheduling system associated with the medical practitioner to schedule an appointment. As shown in the figure, the GUI illustrated in screenshot 810 is similar to the GUI illustrated in screenshot 800, but it includes additional buttons. Specifically, next to the summary of the condition the GUI of the interactive application includes a "more" button 812 for providing additional information on skin feature 134 and statistics of similar types of skin features. The GUI of the interactive application may further include a "schedule" button 814 for opening a window 816 that enables user 110 to pick a date for the appointment with Dr. Shepperd. The dates highlighted in the calendar are dates that Dr. Shepperd has availability in his schedule. After user 110 has selected the date for the appointment, he or she may continue by pressing the "continue" button 818.

In the example depicted in third screenshot 820, the interactive application requests lifestyle data from user 110 in response to a determination that the level of effectiveness of the medical treatment is below a threshold. Processing device 202 may compare the lifestyle data with information stored in a data structure (e.g., data structure 146) to determine the at least one action to alter the medical treatment. As shown in the figure, the GUI illustrated in screenshot 820 is similar to the GUI illustrated in screenshot 800, but a lifestyle questionnaire 822 is provided before a medical action is determined. In one embodiment, the determined action to alter the medical treatment may include a recommendation to change at least one aspect of the lifestyle of user 110. In another embodiment, the determined action to alter the medical treatment may not be associated with the lifestyle data received from user 110.

In the example depicted in fourth screenshot 830, the interactive application provides a recommendation to user 110 after deciding that the action to alter the medical treatment determined in response to receipt of first and second images failed to bring the level of effectiveness of the medical treatment above the threshold. As shown in the figure, the GUI illustrated in screenshot 830 is similar to the GUI illustrated in screenshot 800, but it indicates that an additional third image 130C was received. In the example depicted in fourth screenshot 830, the processing device determined another action to alter the current medical treatment based on the condition of the wound as depicted in third image 130C relative to second image 130B. In some embodiments, system 100 may determine a plurality of medical actions to be completed during a time period. The processing device may identify a most urgent medical action out of the plurality of medical actions based on the determined condition of the skin feature and initiate a measure associated with the most urgent medical action. For example, in the illustrated example, the processing device may determine that removing inflamed tissue is more important than changing a type of wound dressing. Accordingly, the processing device causes the mobile communications device to display information associated with removing inflamed tissue.

Figure 9:
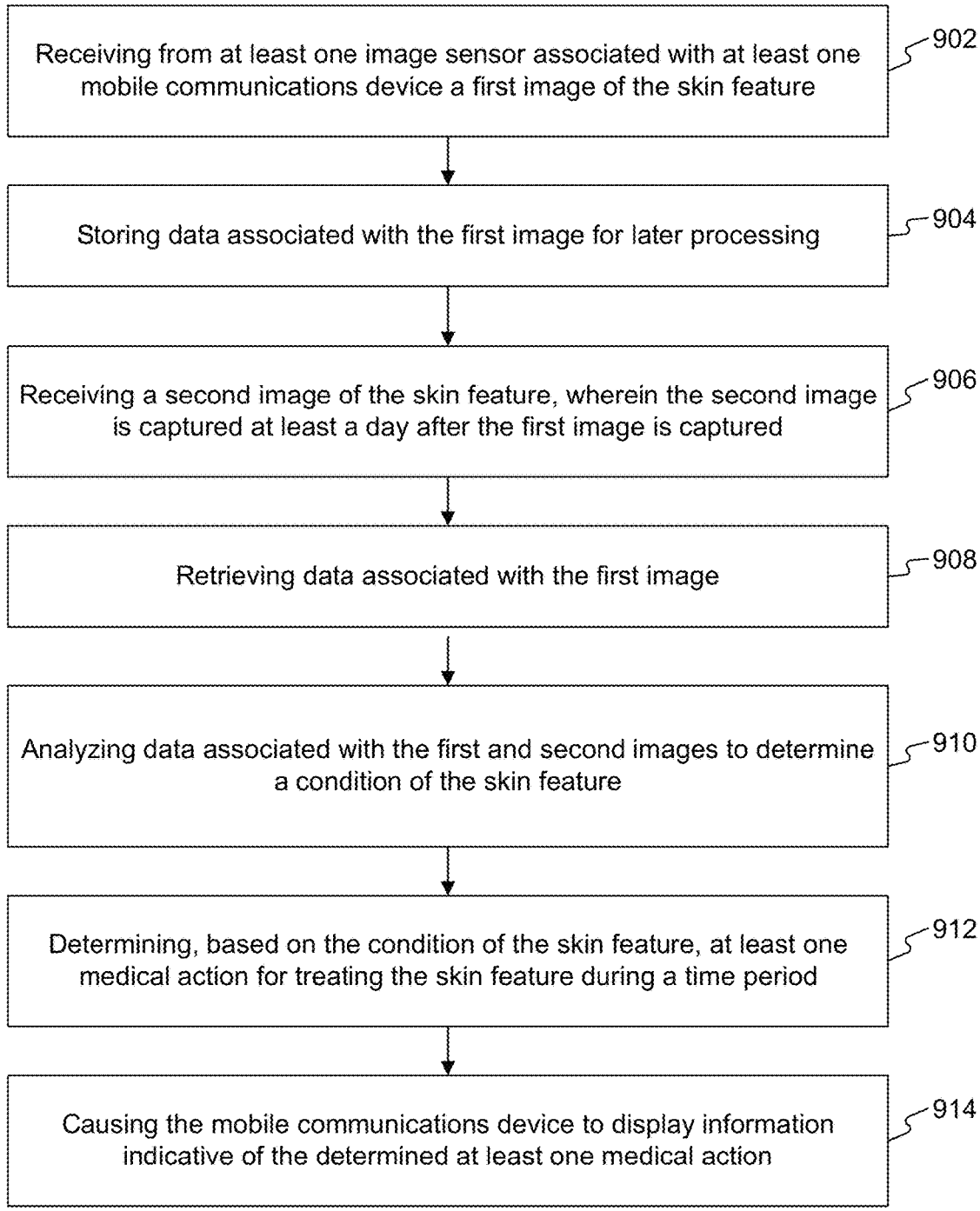
FIG. 9 is a flowchart of a process for conducting image processing of skin features, consistent with the present disclosure.

FIG. 9 is a flowchart of an example process 900 for conducting image processing of skin features executed by a processing device of system 100, according to embodiments of the present disclosure. The processing device of system 100 may include a processor within a mobile communications device (e.g., mobile communications devices 115 and 125) or a processor within a server (e.g., server 145) remote from the mobile communications device. For purposes of illustration, in the following description, reference is made to certain components of system 100. It will be appreciated, however, that other implementations are possible and that any combination of components or devices may be utilized to implement the exemplary method. It will also be readily appreciated that the illustrated method can be altered to modify the order of steps, delete steps, or further include additional steps, such as steps directed to optional embodiments.

Disclosed embodiments may include "receiving from at least one image sensor associated with a mobile communications device a first image of the skin feature." As discussed earlier, various types of image sensors/mobile communications devices may be used to capture different forms of skin features. The skin feature captured by the least one image sensor (e.g., skin feature 134) may have multiple segments of differing colors and differing sizes. Consistent with the present disclosure, the first image may be captured using a mobile communications device having a plurality of image sensors. The first image and/or the image-related information based on the first image may be received at a processor, regardless of where the processor is located. By way of example only, at step 902 in FIG. 9, a processing device (e.g., processing device 202) may receive from at least one image sensor associated with at least one mobile communications device a first image of the skin feature.

Disclosed embodiments may further include "storing in at least one memory device data associated with the first image for later processing." The at least one memory device may include any memory devices associated with system 100, for example, memory device 234 or data structure 146. The data stored at the memory device may include image data associated with the first image and metadata information associated with the first image. As discussed earlier, the image data may include pixel data streams, digital images, digital video streams, data derived from captured images, and data that may be used to construct a 3D image. Consistent with the present disclosure, the image data associated with the first image may include values of parameters indicative of the colors and two/three dimensional measurements of different segments of skin feature 134 (e.g., length, size, depth, volume, shape characteristics, and more). The metadata information may include a device identifier (e.g., based on a MAC address, IP address, port number, serial number, etc.) associated with the device that captured the first image, user identification information (a name, address, phone number, social security number, insurance number, username, medical test number, etc.), patient information, a medical condition, a wound type, information associated with a medical professional (e.g., name of a primary care physician or wound specialist), a country of residence of the user, and/or a timestamp. By way of example only, at step 904 in FIG. 9, the processing device may store data associated with the first image for later processing.

Disclosed embodiments may further include "receiving from the at least one image sensor associated with the mobile communications device a second image of the skin feature, wherein the second image is captured at least a day after the first image is captured." As discussed earlier, the second image may be captured more than a day and less than a month after the first image was captured, more than a week and less than a year after the first image was captured, or any other time period. Consistent with the present disclosure, the first image and the second image were captured by a same mobile communications device. Alternatively, the first image was captured by a first mobile communications device and the second image was captured by a second mobile communications device. For example, during the time between capturing of the first image and capturing of the second time, user 110 may have replaced his or her phone. By way of example only, at step 906 in FIG. 9, the processing device may receive a second image of the skin feature, wherein the second image is captured at least a day after the first image is captured.

Disclosed embodiments may further include "retrieving from the at least one memory device data associated with the first image." As discussed earlier, the processing device may use a database access module (e.g., database access module 612) to retrieve data from a database. The retrieved data may include at least part of the image data associated with the first image. For example, values of parameters indicative of the colors and two/three dimensional measurements of different segments of skin feature 134. Due to possible progression of the skin feature (e.g., such as healing, in case the skin feature is a wound) several changes may have occurred during the time lapse from the capture of the first image to the capture of the second image, for example, the shape, the tissue composition, and/or the color of one or more of the segments may have changed. Therefore, retrieving data associated with the first image may include confirming that the retrieved data associated with the first image refers to a same skin feature depicted in the second image. For example, image analysis of retrieved image data may use location, relative size, distinct features, or other characteristics to confirm that the first image and the second image refer to the same skin feature. Additionally, comparison of metadata information, such as device identifier, may also be used to confirm that the first image and the second image refer to the same skin feature. By way of example only, at step 908 in FIG. 9, the processing device may retrieve data associated with the first image.

In optional embodiments not presented in process 900, each of the first image and the second image may depict the skin feature in proximity to at least one form of colorized surface (e.g., colorized surface 132) having colored reference elements (e.g., colored reference elements 405). In these optional embodiments, the processing device may use the at least one form of colorized surface to determine local illumination conditions (and/or image capturing settings) at a time of capture of the first image and at a time of capture of the second image. In a first example, the at least one form of colorized surface may include a printed form and wherein a same copy of the printed form appears in both the first image and the second image. In a second example, the at least one form of colorized surface may include a printed form and wherein differing copies of the printed form appears in both the first image and the second image. In a third example, the first and second images may depict differing forms of colorized surfaces with a same arrangement of colored reference elements. Consistent with these optional embodiments, the processing device may use the first image, the second image, and the determined local illumination conditions for determining the changes over time of multiple segments of the skin feature (e.g., segments 502). In one example, the processing device may rectify the second image by changing a color of at least one segment of the skin feature as depicted in the second image based on the determined local illumination conditions. Then, using the first image and the rectified second image, the processing device may determine the changes over time of the multiple segments. Alternatively, the processing device may rectify the first image by changing a color of at least one segment of the skin feature as depicted in the first image based on the determined local illumination conditions. Then, in a similar manner, the processing device may use the rectified first image and the second image for determining the changes over time of the multiple segments.

Disclosed embodiments may further include "analyzing the retrieved data and data associated with the second image to determine a condition of the skin feature based on changes over time of the multiple segments." In some examples, the skin feature may be a wound including multiple segments, and determining the condition of the skin feature may include determining a healing progress of the wound by identifying changes over time of geometrical parameters and colors of the multiple segments of the wound. The processing device may use one or more software modules (e.g., image analysis module 606 and medical condition determination module 608) that implement a machine learning model to determine the condition of the skin feature. The machine learning model may use training examples of pairs of images of skin features to analyze the depiction of the skin feature in the first image and the depiction of the skin feature in the second image to determine the condition of the skin feature. An example of such training examples may include a pair of images of a skin feature, together with a label indicating the condition of the skin feature. In some examples, a machine learning model may be trained using training examples to determine conditions of skin features from pairs of image-related information records, and the trained machine learning model may be used to analyze image-related information based on the first image (such as image 130A) and image-related information based on the second image (such as image 130B) determine the condition of the skin feature. Such training examples may include a pair of image-related information records, together with a label indicating the condition of the skin feature, a portion of an image, color information associated with an image, and/or any other data capable of training a machine to determine a condition of a skin feature. By way of example only, at step 910 in FIG. 9, the processing device may analyze data associated with the first and second images to determine a condition of the skin feature based on changes over time of the multiple segments. In some embodiments, a convolution of pixels of the first image may be calculated, a convolution of pixels of the second image may be calculated, and the calculated convolution of pixels of the first image and the calculated convolution of pixels of the second image may be used to determine the condition of the skin feature. For example, a function of the calculated convolution of pixels of the first image may be compared with a function of the calculated convolution of pixels of the second image, in response to a first result of the comparison, a first condition of the skin feature may be determined, and in response to a second result of the comparison, a second condition of the skin feature may be determined, the second condition differs from the first condition.

Consistent with the present disclosure, determining the condition of the skin feature may include predicting an expected appearance (e.g., an expected color, expected size, expected shape, etc.) of the segments of the skin feature at a time of capturing the second image. Disclosed embodiments may include determining a time difference between the first image and the second image. For example, predicting an expected appearance of a skin feature may involve determining a time difference between a capture time of a first image and a capture time of a second image, which may be accomplished by determining a time lapse between image capture. For example, a processing device may determine when an image was captured by reading a timestamp associated with the received images. In cases where a timestamp is superimposed on an image, the processing device may use optical character recognition to read the timestamp. In other embodiments, such as when a timestamp is embedded into an image or attached to it within metadata information, the processing device may extract it from those sources. In some disclosed embodiments, the time difference between the first image and the second image may be determined automatically using metadata information. For example, the time difference between the first image and the second image may be determined automatically by comparing metadata associated with the first image and metadata associated with the second image.

Disclosed embodiments may include further "determining, based on the determined condition of the skin feature, at least one medical action for treating the skin feature during a time period." The processing device may use a software module (e.g., action determination module 610) to determine the at least one medical action based on the changes over time of the multiple segments as reflected in the first and second images. In some embodiments, the determination may further be based on at least one of: a patient's personal medical record, demographic information associated with the patient, and treatment data associated with the skin feature. As discussed earlier, the processing device may also determine the time period for completing the at least one medical action based on the determined condition of the skin feature. The determination of the time period may be based on at least one of the capturing time of the second image (e.g., time elapsed since the capturing, time in day of the capturing, etc.), the type of the determined at least one medical action, a patient's personal medical record, demographic information associated with the patient, and treatment data associated with the skin feature. Alternatively, the processing device may receive an indication of the time period for completing the at least one medical action (e.g., the indication may be received from a medical practitioner of the patient). By way of example only, at step 912 in FIG. 9, the processing device may determine, based on the condition of the skin feature, at least one medical action for treating the skin feature during a time period.

In an optional embodiment, the at least one medical action includes monitoring the condition of the skin feature by capturing a third image of the skin feature at least one day after the second image was captured. For example, the processing device may determine that the skin feature should be captured again in the next three months for monitoring potentially cancerous features or developments. In some cases, the processing device may analyze the first image and the second image to determine recommended image capturing parameters for capturing the third image of the skin feature using the at least one image sensor. For example, the processing device may determine that a flash should be avoided when capturing the third image. Thereafter, the processing may cause a configuration of the at least one image sensor according to the determined capturing parameters. In addition, the processing device may cause the mobile communications device to send a notification indicative of the determined at least one medical action to a user. The notification may include a link for opening an application for capturing the third image of the skin feature. In related embodiments, the processing may determine a time for capturing the third image and predict an appearance of the skin feature at the determined time. Upon receiving the third image of the skin feature, the processing device may determine an additional medical action for treating the skin feature and an additional time period for completing the additional medical action, based on the predicted appearance of the skin feature and an actual appearance of the skin feature as depicted in the third image.

Disclosed embodiments may further include "causing the mobile communications device to display information indicative of the determined at least one medical action." In some cases, the at least one medical action includes treating the skin feature by applying a medicine to the skin feature. In these cases the processing device may cause the mobile communications device to issue a plurality of reminders to apply the medicine to the skin feature over a treatment period extending at least three days after capture of the second image. Additionally, the processing device may cause the mobile communications device to issue a first notification at an outset of the time period and to issue a second notification at a later time during the time period. In one example, the first notification may be identical to the second notification. Alternatively, the first notification may differ from the second notification. As discussed above, causing the mobile communications device to display information indicative of the determined medical action may be one of the measures associated with the determined action initiated by the processing device. Other measures may include updating an electronic medical record of the user, informing that the user is entitled to a different insurance status, schedule an appointment with a medical practitioner, and more. For example, the processing device may access a scheduling system associated with a medical practitioner of a patient having the skin feature to schedule an appointment with the medical practitioner. In this example, the processing device may cause the mobile communications device to cause a display of an addition of a calendar event for the at least one medical action at a date of the scheduled appointment. By way of example only, at step 914 in FIG. 9, the processing device may cause the mobile communications device to display information indicative of the determined at least one medical action.

In optional embodiments not depicted in FIG. 9, the processing device may determine that the at least one medical action was not completed during the time period. Thereafter, the processing device may determine an additional medical action for treating the skin feature and an additional time period for completing the additional medical action. The additional medical action may be the same as the original medical action or different from the original medical action. In some cases, the determination of the additional medical action may be based on the time passed since the capturing of the second image, may be based on the at least one medical action, may be based on the determined time period, may be based on the determined condition of the skin feature and so forth. Similarly, the determination of the additional time period for completing the additional medical action may be based on the additional medical action, may be based on the time passed since the capturing of the second image, may be based on the at least one medical action, may be based on the determined condition of the skin feature and so forth. In other embodiments, the processing device may determine a plurality of medical actions to be completed during the determined time period. The processing device may identify a most urgent medical action out of the plurality of medical actions based on the determined condition of the skin feature and initiate a measure associated with the most urgent medical action. For example, the processing device may cause the mobile communications device to display information indicative of the most urgent medical action.

Consistent with the present disclosure, the first image received in step 902 may be captured before a medical treatment was applied to the skin feature, and the second image of the skin feature received in step 906 may be captured after the medical treatment was applied to the skin feature. In this case, the processing device may determine to alter the medical treatment. For example, the processing device may determine an effectiveness level of the medical treatment by comparing image data associated with changes between the first image and the second image. When effectiveness level is below a threshold, the processing device may determine that at least one medical action for altering the medical treatment needs to be taken. Additional details on this embodiment are discussed below with reference to FIG. 10.

Figure 10:
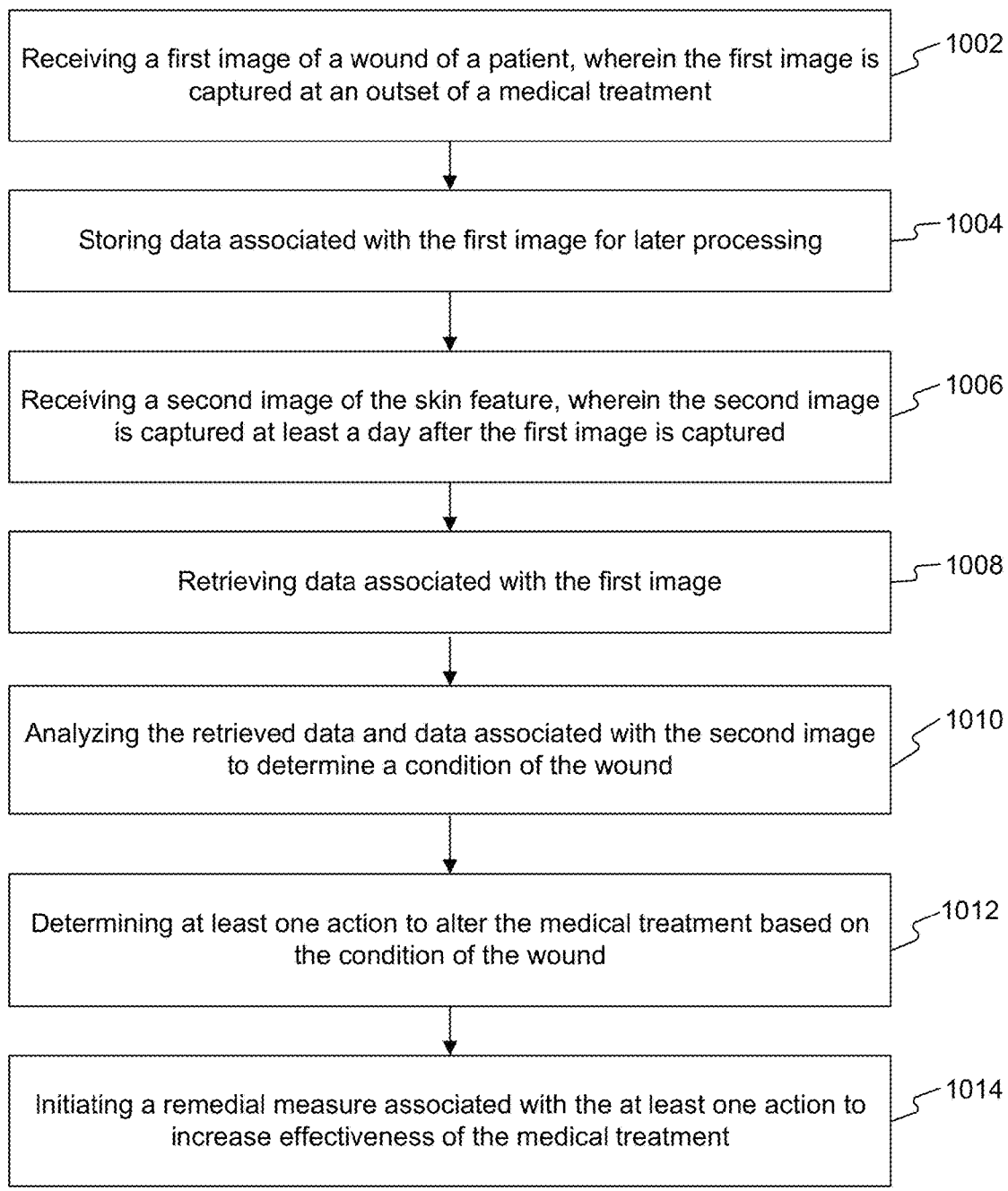
FIG. 10 is a flowchart of a process for conducting image processing of wound images, consistent with the present disclosure.

FIG. 10 is a flowchart of an example process 1000 for conducting image processing of wound images executed by a processing device of system 100, according to embodiments of the present disclosure. The processing device of system 100 may include a processor within a mobile communications device (e.g., mobile communications devices 115 and 125) or a processor within a server (e.g., server 145) remote from the mobile communications device. For purposes of illustration, in the following description, reference is made to certain components of system 100. It will be appreciated, however, that other implementations are possible and that any combination of components or devices may be utilized to implement the exemplary method. It will also be readily appreciated that the illustrated method can be altered to modify the order of steps, delete steps, or further include additional steps, such as steps directed to optional embodiments.

Disclosed embodiments may include "receiving a first image of a wound of a patient, wherein the first image is captured at an outset of a medical treatment." As discussed earlier, various types of image sensors/mobile communications devices may be used to capture different types of wounds. The first image of the wound (e.g., image 130A) may be captured at an outset of a medical treatment. As a person skilled in the art would recognize, a medical treatment may include multiple steps and/or multiple stages. Accordingly, the term "the first image is captured at an outset of a medical treatment" may mean that the first image was captured before any step of the medical treatment was initiated (or completed) or before a given step of the medical treatment was initiated (or completed). For example, the medical treatment may include applying a first ointment on the skin feature for 5 days and then applying a second ointment on the skin feature once or twice a day for 1 to 2 weeks. In the foregoing example, the first image may be captured before the first ointment was applied on the skin feature or before the second ointment was applied on the skin feature. By way of example only, at step 1002 in FIG. 10, a processing device (e.g., processing device 202) may receive a first image of a wound of a patient, wherein the first image is captured at an outset of a medical treatment.

As discussed above with reference to step 904, disclosed embodiments may further include "storing in at least one memory device data associated with the first image for later processing." The data stored in the at least one memory device may include image data and metadata information. Accordingly, at step 1004 in FIG. 10, the processing device may store data associated with the first image for later processing. Disclosed embodiments may further include "receiving a second image of the wound of the patient, wherein the second image is captured at least a day after applying the medical treatment to the wound." As discussed above, the second image may be captured more than a day and less than a month after applying the medical treatment to the wound, more than three days and less than two weeks after applying the medical treatment to the wound, more than a week and less than a year after applying the medical treatment to the wound, or any other time period. Consistent with the present disclosure, the first image and the second image were captured by a same mobile communications device. Alternatively, the first image was captured by a first mobile communications device, and the second image was captured by a second mobile communications device. For example, the first image was captured by a medical practitioner of user 110 (e.g., before treating and dressing the wound), and the second image was captured by user 110 at his or her home. By way of example only, at step 1006 in FIG. 10, the processing device may receive a second image of the wound of the patient, wherein the second image is captured at least a day after applying the medical treatment to the wound.

As discussed above with reference to step 908, disclosed embodiments may further include "retrieving from the at least one memory device, data associated with the first image." The data retrieved from the at least one memory device may include at least part of the image data associated with the first image and/or at least part of the metadata information associated with the first image. Accordingly, at step 1008 in FIG. 10, the processing device may retrieve data associated with the first image. In some embodiments, each of the first image and the second image may depict the wound in proximity to at least one form of colorized surface having colored reference elements. In these optional embodiments, the processing device may use the at least one form of colorized surface (e.g., colorized surface 132) to determine local illumination conditions at a time of capture of the first image and at a time of capture of the second image. In a first example, the at least one form of colorized surface may include a printed form and wherein a same copy of the printed form appears in both the first image and the second image. In a second example, the at least one form of colorized surface may include a printed form and wherein differing copies of the printed form appears in both the first image and the second image. In a third example, the first and second images may depict differing forms of colorized surfaces with a same arrangement of colored reference elements. Consistent with these optional embodiments, the processing device may use the first image, the second image and the determined local illumination conditions for determining the changes over time of multiple segments of the wound. In one example, the processing device may rectify the second image by changing a color of at least one segment of the wound as depicted in the second image based on the determined local illumination conditions. Then, using the first image and the rectified second image the processing device may determine the changes over time of the multiple segments of the wound. Alternatively, the processing device may rectify the first image by changing a color of at least one segment of the wound as depicted in the first image based on the determined local illumination conditions. Then, in a similar manner, the processing device may use the rectified first image and the second image for determining the changes over time of the multiple segments.

Also, as discussed above with reference to step 910, disclosed embodiments may further include "analyzing the retrieved data and data associated with the second image to determine a condition of the wound." In one embodiment, analyzing the retrieved data and the data associated with the second image to determine the condition of the wound may include performing comparative image processing to confirm that a same wound was captured in the first image and the second image and detecting wound image changes over time. By way of example only, the processing device may determine the condition of the wound by assessing the wound progression and its healing progress. Specifically, an artificial neural network (such as deep neural network, convolutional neural network, etc.) may be configured (for example, manually, using machine learning methods, by combining other artificial neural networks, etc.) to determine the condition of the wound based on detected changes of the wound between the first and second images. These changes may include one or more of: changes in dimensions of the wound, changes in composition of tissue type within the wound, changes to the peri-wound skin, changes in surface features, changes in color, changes in texture, changes in other characteristics, or any combination thereof. Accordingly, at step 1010 in FIG. 10, the processing device may analyze the retrieved data and data associated with the second image to determine a condition of the wound. In some embodiments, a convolution of pixels of the first image may be calculated, a convolution of pixels of the second image may be calculated, and the calculated convolution of pixels of the first image and the calculated convolution of pixels of the second image may be used to determine the condition of the wound. For example, a function of the calculated convolution of pixels of the first image may be compared with a function of the calculated convolution of pixels of the second image, in response to a first result of the comparison, a first condition of the wound may be determined, and in response to a second result of the comparison, a second condition of the wound may be determined, the second condition differs from the first condition.

Disclosed embodiments may include "analyzing the retrieved data and data associated with the second image to determine a level of effectiveness of the medical treatment." The term "level of effectiveness of the medical treatment" refers to any indication, numeric or otherwise, of a level (e.g., within a predetermined range) indicative of the healing progress of a skin feature that being medically treated. For example, the effectiveness level may have a value between 1 and 10. Alternatively, the effectiveness level may be expressed as a percentage or any other numerical or non-numerical indication. In some cases, the system may compare the effectiveness level of the medical treatment to a threshold. The term "threshold" as used herein denotes a reference value, a level, a point, or a range of values. In operation, when the level of effectiveness of the medical treatment level exceeds a threshold (or below it depending on a particular use case), the system may follow a first course of action and, when the effectiveness level is below it (or above it, depending on a particular use case), the system may follow a second course of action. The value of the threshold may be predetermined for each type of skin feature or may be dynamically selected based on different considerations such as the user's medical history.

Consistent with the present disclosure, the processing may determine a level of effectiveness of the medical treatment by predicting an expected appearance (e.g., an expected color, an expected size, an expected shape, etc.) of the wound at a time of capturing the second image and comparing the actual appearance with the expected appearance. Disclosed embodiments may include determining a time difference between the first image and the second image. For example, predicting an expected appearance of a wound may involve determining a time difference between a capture time of a first image and a capture time of a second image, which may be accomplished by determining a time lapse between image capture. For example, the processing device may determine when an image was captured by reading a timestamp associated with the received images. In embodiments where a timestamp is superimposed on an image, the processing device may use optical character recognition to read the timestamp. In other embodiments, such as when a timestamp is embedded into an image or attached to it within the metadata information, the processing device may extract it from those sources. In some disclosed embodiments, the time difference between the first image and the second image may be determined automatically using metadata associated with the second image. For example, a processing device may determine the time difference automatically using metadata information associated with the second image. In some disclosed embodiments, the time difference between the first image and the second image may be determined automatically by comparing metadata associated with the first image and metadata associated with the second image.

Based on a time difference between images of a wound, the processing device may determine an expected appearance of the wound. For example, data may be maintained in a data structure that maps a healing process of a wound based on wound characteristics. Alternatively, learning algorithms may be applied to a repository of wound images to identify wounds that most closely correspond to the first image, and thereby predict how the current wound is expected to heal over time. A person skilled in the art would recognize that the predicted expected appearance of the wound may be based on a type of the wound. For example, a laceration is different in type from a burn, and therefore, the healing process for laceration would be expected to be different than a burn. Indeed, there are many different types of wounds, ranging from chemical burns, sunburns, lacerations, abrasions, contusions, hematomas, punctures, and avulsions. Each has its own wound healing profile. In addition, the predicted expected appearance may be based not only on the type of a wound but also on its extent. For example, larger or deeper wounds would be expected to have a different healing process than small or shallower wounds. Since the time lapse is known for the first and second image, based on how other similar wounds of others have healed over time, the system can determine if the wound healing is progressing as expected, or if there appears to be an abnormality. The healing progress may be based on any combination of a change in color of the wound, a reduction in size of the wound, a change in the shape of the wound, a change in the color of an outline of the wound, a change in the tissue composition of the wound, and/or non-wound-related characteristics, such as a patient's age, gender, health, genetics, skin type, or any other non-wound-related characteristic that might correlate to wound healing. The determined healing progress of a wound being medically treated is indicative of the level of effectiveness of the medical treatment. It is to be understood that herein any reference to a healing of a wound (such as healing progress) may also refer to a worsening in the condition of the wound.

In one embodiment, the processing device may analyze the retrieved data and data associated with the second image to determine whether a level of effectiveness of the medical treatment is below a threshold. In response to a determination that the level of effectiveness of the medical treatment is below the threshold, the processing device may initiate the remedial measure associated with the at least one action. In some cases, wherein when the level of effectiveness of the medical treatment is determined to be below the threshold, the processing device may electronically receive lifestyle data from the patient. By way of example, the lifestyle data may include at least one of: information about a diet of the patient, information about sleeping habits of the patient, information about physical activities of the patient, and information about sanitation and hygiene in an environment of the patient. After obtaining the lifestyle data, the processing device may compare the lifestyle data with information stored in a data structure and determine the at least one action to alter the medical treatment. In accordance with this embodiment, the at least one action to alter the medical treatment may include a recommendation to change at least one aspect of the lifestyle of the patient. But in response to a determination that the level of effectiveness of the medical treatment is above the threshold, the processing device may forgo initiating the remedial measure associated with the at least one action. Alternatively, in response to a determination that the level of effectiveness of the medical treatment is above the threshold, the processing device may determine a time period for capturing a third image to continue monitoring the condition of the wound, and output an indication of the determined time period.

Disclosed embodiments may further include "determining at least one action to alter the medical treatment based on the condition of the wound." Consistent with the present disclosure, the processing device may use an artificial neural network (such as deep neural network, convolutional neural network, etc.) to determine the at least one action to alter the medical treatment. The artificial neural network may be configured manually, using machine learning methods, or by combining other artificial neural networks, etc. By way of example only, the at least one action to alter the medical treatment may include increasing a number of times that the wound is cleaned (e.g., once a day, twice a day, once a week, etc.), removing dead or inflamed tissue, changing a type of wound dressing (e.g., films dressings, gauze dressings, hydrogel dressings, hydrocolloid dressings, dressings containing silver or alginates, foam dressings), initiating an antibiotics regime, changing a type or dose of antibiotics, suggesting a wound therapy (e.g., hyperbaric oxygen therapy, ultrasound and electromagnetic therapy, negative pressure wound therapy), and suggesting skin grafts. Accordingly, at step 1012 in FIG. 10, the processing device may determine at least one action to alter the medical treatment based on the condition of the wound.

In an optional embodiment, the processing device may receive a third image of the wound of the patient. The third image may be captured at least a day after information indicative of the at least one action to alter the medical treatment was displayed to the patient. For example, the third image may be captured two days, three days, four days, after the information was displayed to the patient. The processing device may analyze the second image and the third image to determine that the at least one action to alter the medical treatment failed to bring a level of effectiveness of the medical treatment above a threshold. The value of threshold may be determined based on the type of wound, the type of the at least one action previously determined to alter the medical treatment, the time lapse since information on the at least one action was displayed to the patient, and more. Thereafter, the processing device may determine at least one additional action to alter the medical treatment (again), and initiate a further remedial measure associated with the at least one additional action to increase the effectiveness of the medical treatment. The scenario presented in screenshot 830 illustrates this embodiment. In a related embodiment, the processing device may analyze the second image and the third image to determine that the at least one action to alter the medical treatment was incorrectly implemented. For example, after analyzing the first and second images, the processing device may determine that the wound should be kept dressed. But analysis of the third image shows that the wound was left exposed to open air. Thereafter, the processing device may initiate a further remedial measure associated with the at least one action to increase effectiveness of the medical treatment.

Disclosed embodiments may further include "initiating a remedial measure associated with the at least one action to increase effectiveness of the medical treatment." In a first embodiment, initiating the remedial measure may include causing a display of information indicative of the at least one action to alter the medical treatment, for example, screenshot 830. In another embodiment, initiating the remedial measure may include causing a communications device associated with the patient to output an alert associated with the at least one action. In yet another embodiment, initiating the remedial measure may include causing a network transmission, via a communications device of the patient (e.g., user 110), of an alert associated with the at least one action to networked computing device of a medical practitioner (e.g., mobile communications device 125). The alerts may be provided to the patient or the medical practitioner visually, textually, audibly, through an external device, to an external device, and so forth. By way of example only, at step 1014 in FIG. 10, the processing device may initiate a remedial measure associated with the at least one action to increase effectiveness of the medical treatment.

Consistent with the present disclosure, the processing may determine that the data associated with the first and second images is insufficient to determine the condition of the wound. Thereafter, the processing device may cause a display of a request for capturing a third image. In one embodiment, the processing device may cause a display of a request for capturing a third image with or without an image filter. The image filter may be a physical filter for a lens associated with the image sensor. Alternatively, the image filter may be a digital filter applied to the captured image. For example, the image sensor capturing the first and second image may be CCD or CMOS sensors. These type of sensors cover the spectral range around 300-1000 nm (Visible range are around 400-700 nm). In some mobile communication devices, additional filters are attached to the image sensors (e.g., R, G, B filters arranged in a Bayer Filter Mosaic and possibly UV cut and IR cut filters). Consistent with the present disclosure, it may be possible to take IR image with a typical RGB camera by removing IR cut filter. In some embodiments, the processing device may analyze the second image and the third image to determine the condition of the wound and possibly that the level of effectiveness of the medical treatment is below a threshold. In these embodiments, the determination of the condition of the wound may include using image processing to determine an extent of the infection to the wound and/or to determine a type of wound infection. Specifically, the third image, captured using an image filter, may be analyzed to detect an infection to the wound, to determine an extent of the infection to the wound, to determine a type of the infection to the wound, to determine a recommended treatment to the infection to the wound, or any combination thereof. For example, a machine learning model may be trained using training examples to detect infections to wounds, to determine extents of infections to wounds, to determine types of infections to wounds, to recommend treatments to infections to wounds based on images of the wounds. An example of such training examples may include one or more images of a wound, together with an indication of desired detection and/or determination.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, e.g., hard disks or CD ROM, or other forms of RAM or ROM, USB media, DVD, Blu-ray, Ultra HD Blu-ray, or other optical drive media.

Computer programs based on the written description and disclosed methods are within the skills of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The examples are to be construed as non-exclusive. Furthermore, the steps of the disclosed methods may be modified in any manner, including by reordering steps and/or inserting or deleting steps. It is intended, therefore, that the specification and examples be considered as illustrative only.

We claim:

1. A non-transitory computer readable medium for conducting image processing of skin features, the computer readable medium containing instructions that, when executed by a processor, cause the processor to perform a method, the method comprising:
    receiving from at least one image sensor associated with a mobile communications device a first image of the skin feature, the skin feature having multiple segments of differing colors and differing sizes;
    storing in at least one memory device data associated with the first image for later processing;
    receiving from the at least one image sensor associated with the mobile communications device a second image of the skin feature, wherein the second image is captured at least a day after the first image is captured;
    retrieving from the at least one memory device data associated with the first image;
    analyzing the retrieved data and data associated with the second image to determine a condition of the skin feature based on changes over time of the multiple segments;
    determining, based on the determined condition of the skin feature, at least one medical action for treating the skin feature during a time period; and
    causing the mobile communications device to display information indicative of the determined at least one medical action.

2. The non-transitory computer readable medium of claim 1, wherein the skin feature includes a wound including the multiple segments, and determining the condition of the skin feature includes determining a healing progress of the wound by identifying changes over time of geometrical parameters and colors of the multiple segments of the wound.

3. The non-transitory computer readable medium of claim 1, wherein the at least one medical action includes treating the skin feature by applying a medicine to the skin feature, the method further including:
    causing the mobile communications device to issue a plurality of reminders to apply the medicine to the skin feature over a treatment period extending at least three days after capture of the second image.

4. The non-transitory computer readable medium of claim 1, wherein the method further includes determining the time period based on the determined condition of the skin feature.

5. The non-transitory computer readable medium of claim 1, wherein the at least one medical action includes monitoring the condition of the skin feature by capturing a third image of the skin feature at least one day after the second image was captured.

6. The non-transitory computer readable medium of claim 5, wherein the method further includes analyzing the first image and the second image to determine recommended image capturing parameters for capturing the third image of the skin feature using the at least one image sensor.

7. The non-transitory computer readable medium of claim 6, wherein the method further includes causing a configuration of the at least one image sensor according to the determined capturing parameters.

8. The non-transitory computer readable medium of claim 5, wherein causing the mobile communications device to display the information indicative of the determined at least one medical action includes sending a notification to a user, the notification including a link for opening an application for capturing the third image of the skin feature.

9. The non-transitory computer readable medium of claim 5, wherein the method further includes:
    determining a time for capturing the third image;
    predicting an appearance of the skin feature at the determined time for capturing the third image;
    receiving from the at least one image sensor associated with the mobile communications device the third image of the skin feature; and
    based on the predicted appearance of the skin feature and an actual appearance of the skin feature as depicted in the third image, determining an additional medical action for treating the skin feature and an additional time period for completing the additional medical action.

10. The non-transitory computer readable medium of claim 1, wherein the method further includes:
    determining that the at least one medical action was not completed during the time period;
    determining an additional medical action for treating the skin feature; and
    determining an additional time period for completing the additional medical action.

11. The non-transitory computer readable medium of claim 1, wherein the method further includes:
    determining a plurality of medical actions to be completed during the time period;
    identify a most urgent medical action out of the plurality of medical actions based on the determined condition of the skin feature; and
    causing the mobile communications device to display information indicative of the most urgent medical action.

12. The non-transitory computer readable medium of claim 1, wherein determining the at least one medical action is based on the changes over time of the multiple segments as reflected in the first and second images and further based on at least one of: a patient's personal medical record, demographic information associated with the patient, and treatment data associated with the skin feature.

13. The non-transitory computer readable medium of claim 1, wherein the method further includes accessing a scheduling system associated with a medical practitioner of a patient having the skin feature to schedule an appointment with the medical practitioner.

14. The non-transitory computer readable medium of claim 1, wherein causing the mobile communications device to display the information indicative of the determined at least one medical action includes causing the mobile communications device to issue a first notification at an outset of the time period and to issue a second notification at a later time during the time period.

15. The non-transitory computer readable medium of claim 1, wherein each of the first image and the second image depicts the skin feature in proximity to at least one form of colorized surface having colored reference elements, and wherein the method further includes:
   using the at least one form of colorized surface to determine local illumination conditions at a time of capture of the first image and at a time of capture of the second image; and
   using the first image, the second image and the determined local illumination conditions for determining the changes over time of the multiple segments.

16. The non-transitory computer readable medium of claim 15, wherein the at least one form of colorized surface includes a printed form and wherein a same copy of the printed form appears in both the first image and the second image.

17. The non-transitory computer readable medium of claim 15, wherein the at least one form of colorized surface includes a printed form and wherein differing copies of the printed form appears in both the first image and the second image.

18. The non-transitory computer readable medium of claim 1, wherein the first image of the skin feature is captured before applying a medical treatment to the skin feature, and the second image of the skin feature is captured at least a day after applying the medical treatment to the skin feature, and wherein the method further includes:
   determining an effectiveness level of the medical treatment by comparing image data associated with changes between the first image and the second image; and
   when effectiveness level is below a threshold, determining at least one additional medical action to be taken.

19. A method of conducting image processing of skin features, the method comprising:
   receiving from at least one image sensor associated with a mobile communications device a first image of the skin feature, the skin feature having multiple segments of differing colors and differing sizes;
   storing in at least one memory device data associated with the first image for later processing;
   receiving from the at least one image sensor associated with the mobile communications device a second image of the skin feature, wherein the second image is captured at least a day after the first image is captured;
   retrieving from the at least one memory device data associated with the first image;
   analyzing the retrieved data and data associated with the second image to determine a condition of the skin feature based on changes over time of the multiple segments;
   determining, based on the condition of the skin feature, at least one medical action for treating the skin feature during a time period; and
   causing the mobile communications device to display information indicative of the determined at least one medical action.

20. A system for conducting image processing of skin features, the system comprising:
   at least one processor programed to:
      receive from at least one image sensor associated with a mobile communications device a first image of the skin feature, the skin feature having multiple segments of differing colors and differing sizes;
      store in at least one memory device data associated with the first image for later processing;
      receive from the at least one image sensor associated with the mobile communications device a second image of the skin feature, wherein the second image is captured at least a day after the first image is captured;
      retrieve from the at least one memory device data associated with the first image;
      analyze the retrieved data and data associated with the second image to determine a condition of the skin feature based on changes over time of the multiple segments;
      determine, based on the condition of the skin feature, at least one medical action for treating the skin feature during a time period; and
      cause the mobile communications device to display information indicative of the determined at least one medical action.

* * * * *